(12) United States Patent
Sinauridze et al.

(10) Patent No.: US 8,426,433 B2
(45) Date of Patent: *Apr. 23, 2013

(54) ANTICOAGULANT COMPOUNDS, PHARMACEUTICAL COMPOSITIONS ON THEIR BASIS TO TREAT THROMBOTIC CONDITIONS, AND PLASMA-SUBSTITUTING SOLUTION TO CORRECT HYPERCOAGULATION DEFECTS OF HEMODILUTION

(75) Inventors: Elena Ivanovna Sinauridze, Lyubertsy (RU); Fazoil Inoyatovich Ataullakhanov, Moscow (RU); Andrey Alexandrovich Butylin, Moscow (RU); Vladimir Borisovich Sulimov, Moscow (RU); Alexey Nickolayevich Romanov, Moscow (RU); Alexey Alexeevich Bogolyubov, Bologoe (RU); Yury Vladimirovich Kuznetsov, Odintsovo (RU); Irina Vladimirovna Gribkova, Moscow (RU); Alexander Sergeevich Gorbatenko, Moscow (RU); Olga Anatolievna Kondakova, Moscow (RU)

(73) Assignee: Obschestvo S Ogranichennoi Otvetsttvennoctiyu "Bionika", Moscow (RU)

( * ) Notice: Subject to any disclaimer, the term of this patent is extended or adjusted under 35 U.S.C. 154(b) by 280 days.

This patent is subject to a terminal disclaimer.

(21) Appl. No.: 12/666,250

(22) PCT Filed: Jun. 27, 2008

(86) PCT No.: PCT/RU2008/000401
§ 371 (c)(1),
(2), (4) Date: Dec. 22, 2009

(87) PCT Pub. No.: WO2009/002229
PCT Pub. Date: Dec. 31, 2008

(65) Prior Publication Data
US 2011/0003826 A1    Jan. 6, 2011

(30) Foreign Application Priority Data

Jun. 28, 2007 (RU) .................. 2007124202

(51) Int. Cl.
*A01N 43/54* (2006.01)
*A61K 31/505* (2006.01)
(52) U.S. Cl.
USPC ........... 514/275; 514/339; 514/357; 514/370; 514/631; 544/326; 544/328; 546/275.7; 546/311; 548/190; 548/193; 564/244; 564/246

(58) Field of Classification Search ............... 546/274.1, 546/311; 544/296, 328, 326; 548/164
See application file for complete search history.

(56) References Cited

U.S. PATENT DOCUMENTS

| 3,407,229 A | 10/1968 | Regan |
| 5,792,769 A * | 8/1998 | Lu et al. ............. 514/252.12 |
| 5,886,191 A | 3/1999 | Dominguez et al. |
| 2005/0159457 A1 | 7/2005 | Pan et al. |
| 2011/0003826 A1 * | 1/2011 | Sinauridze et al. ...... 514/252.03 |

FOREIGN PATENT DOCUMENTS

| JP | 03041065 A * | 2/1991 |
| JP | 05134337 | 5/1993 |
| JP | 05134337 A * | 5/1993 |
| WO | WO 2005/094828 A1 | 10/2005 |

OTHER PUBLICATIONS

S.L. Morissette et al., Advanced Drug Delivery Reviews, 56, 275-300, 275 (2004).*
J. Aaltonen et al., European Journal of Pharmaceutics and Biopharmaceutics, 71, 23-37, 26 (2009).*
S.R. Byrn et al, Solid-State Chemistry of Drugs, 516 (2nd ed., 1999).*
Gavezzotti, Accounts of Chemical Research, 27, 309-314 (1994).*
B.M. Regan et al., Journal of Medicinal Chemistry, 10, 649-652 (1967).*
CrossFire Beilstein Database, Beilstein Registry No. 3974443.
CrossFire Beilstein Database, Beilstein Registry No. 3976136.
Nanosyn Compound Library, Accession No. 2033827231, Order No. NS9827.
Regan, B.M. et al. 1967 "The 2-Thiopsuedourea Moiety, a New Local Anestesiophore", *Journal of the Mecicinal Chemistry* 10: 649-652.
Scozzafava, A. et al. 1999 "Protease inhibitors—Part 3. Synthesis of non-basic thrombin inhibitors incorporating pyridinium-sulfanilylguanidine moieties at the P1 site" *Euroepan Journal of Medicinal Chemistry* 34: 939-952.

* cited by examiner

*Primary Examiner* — James O Wilson
*Assistant Examiner* — Alexander R Pagano
(74) *Attorney, Agent, or Firm* — Knobbe Martens Olson & Bear LLP

(57) ABSTRACT

This invention relates to new chemical compounds, application of these compounds as anticoagulants, pharmaceutical compositions, and plasma-substituting solutions on their basis, and can be used for treating thromboembolic complications of diseases such as myocardial infarction, stroke, and thrombosis of deep veins or a pulmonary artery; and for preventing hypercoagulation conditions in consequence of injuries, surgeries, sepsis, various obstetric pathologies, in disaster medicine, resuscitation, and so on.

11 Claims, 6 Drawing Sheets

ANTICOAGULANT COMPOUNDS, PHARMACEUTICAL COMPOSITIONS ON THEIR BASIS TO TREAT THROMBOTIC CONDITIONS, AND PLASMA-SUBSTITUTING SOLUTION TO CORRECT HYPERCOAGULATION DEFECTS OF HEMODILUTION

FIELD OF THE INVENTION

This invention relates to new chemical compounds, application of these compounds as anticoagulants, pharmaceutical compositions, and plasma-substituting solutions on their basis, and can be used for treating thromboembolic complications in diseases such as myocardial infarction, stroke, thrombosis of deep veins or pulmonary artery; and preventing development of hypercoagulation conditions as a result of injuries, surgeries, sepsis, a variety of obstetric pathologies, in disaster medicine, resuscitation, and so on.

BACKGROUND OF THE INVENTION

A great number of diverse pathologies of the organism are caused by disorders in the hemostatic system. Thromboembolic complications developing from diseases such as myocardial infarction, stroke, thrombosis of deep veins or pulmonary artery are among the chief causes of death around the world. Little surprise then that intensive efforts have been going on for years to develop medications that could serve as effective and safe clinical drugs. Above all, these are various antithrombotic agents displaying anticoagulant properties.

Thrombin is the principal enzyme of the blood clotting system converting the soluble plasma protein, fibrinogen, into an insoluble fibrin clot, and, at the same time, setting off a majority of positive and negative feedbacks in the system, activating thrombocytes (platelets), factors V, VIII, and XIII, and also protein C. Thrombin also initiates various cellular and vascular reactions, including proliferation of endothelium cells, ejection of plasminogen activators, and so on. Considering that thrombin is involved in a large number of key bioregulatory events, thrombin inhibition at its active center must be very effective and offer much promise in controlling many patho-physiological conditions.

There are three principal approaches to engage the hemostatic system in order to prevent undesirable thrombosis—using direct and indirect inhibitors of serine proteases in the clotting series (in the first place, thrombin and factor Xa); using antithrombocytic preparations (antagonists GPIIb/IIIa, aspirin, thrombin receptor antagonists, and so on), which reduce the aggregating properties of thrombocytes and, therefore, prevent further clotting; and using vitamin K antagonists, which reduce synthesis of clotting factor precursors in the liver.

Three principal antithrombotic preparations are used in clinics today—unfractionated heparin; oral anticoagulant warfarin (vitamin K antagonist), and aspirin as a thrombocytes aggregation inhibitor. Each of these preparations, however, has limitations in use and produces undesirable side effects.

Unfractionated heparin (UFH) is a natural anionic polysaccharide, a mixture of polysaccharide chains of different lengths constructed from repeating disaccharide units consisting of uronic (L-iduronic and/or D-glucuronic) acid residues and residues of D-glucosamine. Its molecular weight is put differently by different sources at 3,000-5,000 to 30,000-40,000 dalton, peaking at between 12,000 and 15,000 dalton.

Unfractionated heparin and its lighter analogues (low molecular weight heparins, or LMWH) are indirect anticoagulants. They do not inhibit thrombin by themselves, but only enhance the effect of natural plasma clotting inhibitor antithrombin III (ATIII). If, therefore, the ATIII content in a patient's plasma is very low for some reasons, heparins display a weak anticoagulant effect.

Used in clinical practice, unfractionated heparin has a number of failings:
1. Unfractionated heparin has a short-lived effect, which vanishes very quickly after withdrawal from the medication, and UFH cannot lower the risk of repeated thrombotic events.
2. Heparin displays its antithrombotic effect indirectly, and to display it at all, it must be used in the presence of antithrombin in the system
3. Heparin is only active against circulating thrombin, and almost does not inhibit thrombin adsorbed on a clot.
4. An identical dose of heparin has an unpredictable response in different patients for many reasons, including the level of ATIII in plasma, individual preparation injection rate, binding and neutralization of heparin under the effect of different plasma proteins and activated thrombocytes (thrombocytic factor 3, heparinase, and so on). This requires the status of the coagulation system to be monitored at frequent intervals.
5. Risk of hemorrhagic complications and possibility of thrombocytopenia.
6. Osteoporosis is likely to develop as a complication after prolonged heparin therapy (over 6 months) and sufficiently high heparin doses (>15000 units).
7. Heparin can only be injected intravenously in hospital conditions.

Vitamin K antagonists (of warfarin type) are indirect clotting inhibitors as well. The mechanism of the effect these preparations have on the clotting system is due to their capacity to effectively block synthesis of vitamin K-dependent clotting factors in the liver. Post-translational γ-carboxylation of the N terminal end of a future factor is essential for synthesizing a factor molecule. Carboxylation is absolutely required for factor molecules to be bound (through $Ca^{+2}$ ions) during clotting to the negatively charged phospholipid surface of activated thrombocytes and fulfill their function. Vitamin K is an important carboxylation cofactor. During the reaction, it alternates between its hydroxy-quinone form, which is actually involved in the carboxylation reaction, and its oxidized epoxy form. Under the effect of vitamin K reductase enzyme, the epoxy form is reduced and can again be drawn into the carboxylation reaction. Preparations in the coumarin group block the reduction.

Warfarin, too, has several limitations and drawbacks. First, there is slow response to the therapy. It is first observed 24 hours after administration, and gathers full strength within several days. Besides, the preparation binds strongly to various food components and is significantly overlapped by many medications. There is also considerable genetic variability in the activity of the warfarin metabolizing enzyme. This explains significant individuals variability in the response to warfarin, suggesting that certain dietary restrictions and systematic monitoring are required for warfarin recipients.

As we said above, antithrombocytic preparations (aspirin, GPIIb/IIIa antagonists, and so on) hinder complete activation of thrombocytes and their contribution to enhancing the clotting reaction, putting constraints on continued production of thrombin. They do not, however, affect the performance of thrombin that has already formed.

To sum up, all the standard antithrombotic agents surveyed above each have their own drawbacks. Some of them are not direct thrombin inhibitors, requiring antithrombin III (UFH or LMWH) to be present in plasma to have effect, or take effect only slowly, inhibiting the synthesis of essential clotting factors (warfarin and so on), while others (antithrombotic agents) do not affect the thrombin already formed. This explains why intensive search has continued for years for "ideal" inhibitors of much the same efficiency and free from many drawbacks of the standard preparations.

Very attractive in this sense is the strategy of developing small synthetic thrombin inhibitors acting as anticoagulants. These inhibitors have a quick and direct effect on thrombin present in blood, inspiring hope of being effective in controlling acute thrombotic complications even in spite of ATIII shortage in plasma.

The strategic search for new direct synthetic serine protease inhibitors in the clotting series is focused on meeting the following requirements such inhibitor is expected to satisfy:

High affinity to the target enzyme (that is, high inhibiting efficiency).
High selectivity in respect of the target enzyme in comparison with other related serine proteases.
Chemical and metabolic stability.
No toxicity.
Weak (or not very strong) binding to plasma proteins.
High bioavailability when administered through the mouth.
Relatively long half-life of the preparation, allowing, if administered orally, the therapeutic level in plasma to be maintained at a level where one or two preparation intakes a day could be enough.
Possibility of simple monitoring of the preparation level.

Many surveys devoted to the development of low molecular weight thrombin inhibitors have been published by the time of this writing (Shafer J. A., Cardiovascular Chemotherapy: Anticoagulants, Curr. Opin. Chem. Biol., 1998, 2:458-465; Steinmetzer T., Hauptmann J., Sturzebecher J., Advances in the Development of Thrombin Inhibitors, Exp. Opin. Invest. Drugs, 2001, 10(5):845-864; Edmunds J J, Rapundalo S T, Siddiqui M A, Thrombin and Factor Xa Inhibition, Ann. Rep. Med. Chem., 1996, 31:51-60; Wiley M. R., Fisher M. J., Small Molecule Direct Thrombin Inhibitors, Expert Opin. Ther. Patents, 1997, 7:1265-1282; Hauptmann J, Sturzebecher J., Synthetic Inhibitors of Thrombin and Factor Xa: from Bench to Bedside, Thromb. Res., 1999, 93(5): 203-241; Vacca J P., New Advances in the Discovery of Thrombin and Factor Xa Inhibitors, Curr. Opin. Chem. Biol., 2000, 4(4):394-400).

Developing medications on the basis of new chemical compounds, however, requires, in addition to assessing their possible pharmacological effect, careful testing of the toxicological properties of the preparations and their possible effect on heredity, and identifying other remote consequences of their application.

This task is complicated by the fact that far from each inhibitor reducing thrombin activity in buffering aqueous solutions can serve as a real anticoagulant to control blood clotting in the organism. This could be related, for example, to the inhibition mechanism. In particular, unless the inhibitor is competitive, enzymatic activity would not be suppressed completely even if all 100% active centers of plasma thrombin are bound to such inhibitor. Residual thrombin activity may be low enough, but in certain cases it cannot be fully suppressed in plasma by the natural thrombin inhibitor—ATIII. This happens because of a certain modification of the thrombin molecule conformation when bound to such inhibitor, which prevents ATIII from approaching the active thrombin center. As a result, blood continues to be exposed to residual thrombin activity for a long time, and the integral coagulation response, far from falling, even can ultimately intensify because of the presence of this compound in the organism. If the prospective thrombin inhibitor reacts with other components of the clotting system (factors or clotting inhibitors), the ultimate response of the system is impossible to predict in advance as well. The strong bond between the inhibitor and various plasma proteins may increase considerably the dose that must be administered to the organism to achieve the desired anticoagulation effect.

With consideration for the aforesaid, it is clear why, with so large a number of synthesized compounds capable of inhibiting thrombin now available, only one—Argatroban, a thrombin inhibitor synthesized in Japan—has passed all necessary tests and has effectively been authorized in clinical practice (U.S. Pat. No. 5,214,052, 1993; Schwarz R. P., The Preclinical and Clinical Pharmacology of Novastan (Argatroban), In: "New Anticoagulants for the Cardiovascular Patient," Pifarre R., editor, Hanley and Belfus, Inc., Philadelphia, Pa., U.S., 1997, pp. 231-249; Okamoto S, Hijikata A, Kikumoto R, Tonomura S, Hara H, Ninomiya K, Maruyama A, Sugano M, Tamao Y., Potent Inhibition of Thrombin by the Newly Synthesized Arginine Derivative No. 805. The Importance of Stereo-Structure of its Hydrophobic Carboxamide Portion, Biochem. Biophys. Res. Commun. 1981, 101(2): 440-446).

The search for new anticoagulants among synthetic low molecular weight thrombin inhibitors continues to present a defiant challenge.

These inhibitors can be used as anticoagulants directly to treat acute thrombotic conditions developing in the organism in consequence of various pathologies.

Besides, they can also be used to forestall hypercoaguability. This invention proposes to use a synthetic low molecular weight thrombin inhibitor displaying anticoagulant activity in plasma, to be added to a standard plasma-substituting solution.

Frequent situations developing in clinic require large quantities of lost blood to be rapidly replaced with artificial plasma-substituting solutions (PSS). Blood loss is caused by injuries, surgeries, sepsis, various obstetric pathologies, disaster medicine, resuscitation, and so on.

SUMMARY OF THE INVENTION

This invention pursues the following principal objects:

1. Replacing the volume of circulating blood (VCB) to maintain arterial pressure and volume of cardiac output, preventing vascular collapse, and sustaining normal rheological characteristics of blood and normal perfusion of organs and tissues.

2. Maintaining normal colloidal osmotic pressure of plasma and its acid-base equilibrium.

3. Maintaining the oxygen-transport function of blood and clotting system functions.

To achieve the first two objects, it is common practice to transfuse various plasma-substituting solutions and albumin solutions. The oxygen-transport function is fulfilled by transfusion of erythrocytes, modified hemoglobin or oxygen-enduring solutions of perfluorans, and the clotting system functions are maintained by transfusing fresh-frozen plasma (FFP), thrombocyte concentrates, concentrated prothrombin complex factors, or individual clotting factors.

Artificial plasma-substituting solutions are divided into two classes: crystalloidal and colloidal. The first class are salt solutions (for example, 0.9% NaCl solution, the physiological saline), and the second class contains additives of high molecular weight polymers (dextrans, hydroxyethyl starches, gelatin derivatives, and so on).

Large volume infusions of standard PSS result in blood dilution with these solutions (hemodilution). Since none of standard plasma-substituting solutions in use today contains clotting factors and inhibitors, hemodilution lowers the concentrations of clotting system components in blood. It has been shown already that hemodilution developing through massive standard PSS transfusions unbalances the clotting system and intensifies coagulation. This happens because dilution makes the system more sensitive to decline in the concentrations of clotting inhibitors even though procoagulant precursors of the clotting factors are present in significantly excessive quantities in plasma, to the extent that moderate dilutions do not cause decline in their concentrations to have any appreciable effect on the clotting rate. To correct possible hypercoagulation disorders caused by massive PSS transfusions, these inventors have developed a new PSS that includes natural thrombin inhibitor, antithrombin III (Russian patent issued on Application No. 2005140841 by an Office Action of Dec. 27, 2005). The claimed solution is a forerunner of new-generation plasma-substituting solutions capable of partially correcting hypercoagulation disorders caused by massive PSS transfusions. This solution is in no way the best choice because antithrombin III is a natural protein that has to be extracted from human plasma. As such, it is rather expensive and does not rule out the possibility of the preparation being infected by a virus (HIV, hepatitis, etc.). A synthetic low molecular weight thrombin inhibitor, an anticoagulant, can be a good alternative to antithrombin III.

Compounds that are attractive in terms of practical application in the anticoagulant role, that is, are capable of slowing down and/or preventing blood clotting, were selected on the basis of the following criteria:
1. The substance must be a thrombin inhibitor, that is, be capable of preventing thrombin-catalyzed amidolytic reaction in which the fibrinogen molecule is broken down.
2. The substance must have acceptable physicochemical characteristics (lipophily and hydrophily) to be present in blood plasma in an unbound state of sufficient concentration. In other words, it must moderately bind to other blood plasma proteins (albumins, globulins, etc.).
3. The substance must have a sufficiently long lifetime in blood plasma to display its inherent therapeutic effect.

Selection according to the first criterion was made in two steps. First, a virtual library centered on structures described by general structural formula (I) was built, and the resultant structures were docked into the active center of the thrombin molecule. The most likely prospects ("virtual hits"), that is, molecules that registered scoring function readings (measured during the docking process) at least as good as −5.0 kcal/mole, were selected at the end of the first step. The second selection step comprised measuring the direct inhibiting effect of the compounds selected as aforesaid on thrombin activity in an aqueous buffering solution, in which thrombin was breaking down the specific chromogenic (or fluorogenic) substrate. The substrate breakdown reaction rate slowed down in the presence of the inhibitor. Compounds of formula (I), which inhibited thrombin activity in the buffering solution by more than 60%, even if used in sufficiently small concentrations (<1 mM), were selected for subsequent testing of the anticoagulant effect of the new compounds in blood plasma.

The molecules of new thrombin inhibitors that could be effective anticoagulants in the organism were constructed in such a way that, to give the inhibitor molecule acceptable physicochemical properties contributing to a beneficial pharmacokinetics, it is preferred to balance off, to an extent, the hydrophobic nature of the molecule of formula (I) inhibitor as a whole by choosing hydrophilic linkers. Also with the same purpose, it is possible to modify hydrophobic fragments deposited in pocket S3 of the thrombin molecule with hydrophilic residues deposited in the pocket at the side exposed to the solvent.

A sufficient lifetime in blood plasma can be obtained by keeping the inhibitor structure free from labile chemical groups that break down easily in chemical or biochemical processes. An ester group, for example, is an illustration of such unwanted groups.

To conclude, molecules that optimally meet the above criteria (even if contradictory at times) can be selected for chemical synthesis and subsequent experimental testing as anticoagulants.

The final decision to undertake synthesis was made with consideration for its possible complexity.

DETAILED DESCRIPTION OF THE PREFERRED EMBODIMENT

Figure 1:
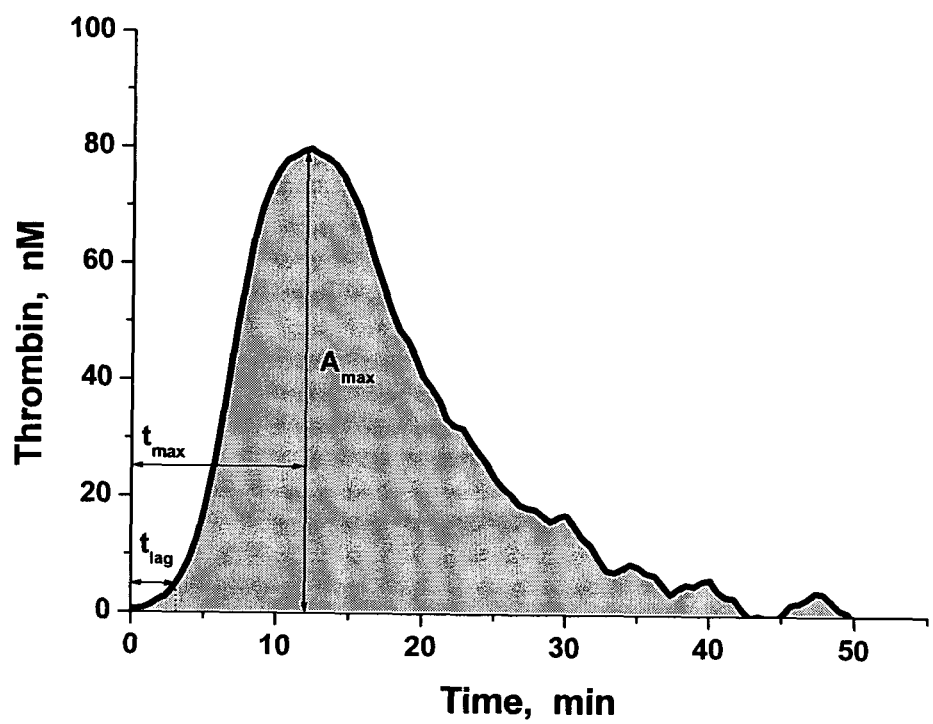
FIG. 1. Kinetics of thrombin generation and loos of plasma after clotting activation.

Unless indicated otherwise, the following definitions are used in this description:

Active center is an area of the protein macromolecule that plays a key role in biochemical reactions.

Protein means a protein macromolecule.

Target protein means a protein macromolecule involved in the binding process.

Ligands means a collection of low molecular weight chemical structures.

Binding process means formation of Van der Waals' or a covalent complex of a ligand and the active center of target protein.

Screening means identification of a set of compounds in a collection of chemical structures that react selectively with a specific area of the protein macromolecule.

Correct positioning means positioning to place a ligand in a position corresponding to the minimum free protein binding energy.

Selective ligand means a ligand that is bound in a specific manner to a particular target protein.

Reference protein means a protein used either to adjust the parameters of a score in accordance with experimental data, or during validation of the operating system, or to assess the binding specificity of a particular inhibitor.

Validation means a series of calculations and comparison methodology to assess the quality of the system in operation and its efficiency in selecting ligands from a random set of ligands that are bound reliably to a given target protein.

Specifically binding ligand means a ligand that is bound to a particular protein only, but not to any other proteins.

Inhibitor means a ligand that is bound to the active center of a particular target protein and blocks the normal course of biochemical reactions.

Docking means the positioning of a ligand in the active center of a protein.

Scoring means calculation to assess the free energy needed to bind a ligand to a protein.

ΔG binding means the resulting free energy calculation gain needed to bind a ligand to a target protein (using the SOL software).

$C_{1-6}$ alkyl means an alkyl group comprising an unbranched or branched hydrocarbon chain with 1 to 6 carbon atoms, for example, methyl, ethyl, n-propyl, isopropyl, n-butyl, isobutyl, tert-butyl, and so on.

$C_{1-6}$ alkoxy means an alkoxy group containing an unbranched or branched hydrocarbon chain with 1 to 6 carbon atoms, for example, methoxy, ethoxy, n-propoxy, isopropoxy, and so. on.

Halogen means chlorine, bromine, iodine, or fluorine.

Pharmaceutically acceptable salt means any salt produced by an active compound of formula (I), unless it is toxic or inhibits adsorption and pharmacological effect of the active compound. Such salt can be produced by reaction between a compound of formula (I) and an organic or inorganic base, such as sodium hydroxide, potassium hydroxide, ammonium hydroxide, methylamine, ethylamine, and the like.

Solvate means the crystalline form of an active compound of formula (I) whose crystalline lattice contains molecules of water or another solvent from which the active compound of formula (I) has crystallized.

Pharmaceutically acceptable carrier means a carrier that must be compatible with the other ingredients of a composition and be harmless to the recipient, that is, be nontoxic to cells or mammals in doses and concentrations in which it is used. Frequently, a pharmaceutically acceptable carrier is an aqueous pH buffering solution. Examples of physiologically acceptable carriers include buffers such as phosphates, citrates, or other salts of organic acids; antioxidants including ascorbic acid, polypeptides of low molecular weight (less than 10 residues); proteins such as serum albumin, gelatin or immunoglobulins; hydrophilic polymers such as polyvinyl pyrrolidone; amino acids such as glycine, glutamine, asparagine, arginine, or lysine; monosaccharides, disaccharides, and other carbohydrates, including glucose, mannose or dextrins; chelating agents such as EDTA; and sugar alcohols such as mannitol or sorbitol.

Therapeutically effective quantity means a quantity needed to achieve the desired therapeutic effect (that is, the desired extent of thrombosis inhibition) in a mammal organism.

Mammal, in the sense in which it is used here, include primates (for example, humans, anthropoid apes, non-anthropoid apes, and lower monkeys), predators (for example, cats, dogs, and bears), rodents (for example, mouse, rat, and squirrel), insectivores (for example, shrew and mole), and so on.

The practical task set by the applicant is achieved by developing new low molecular weight compounds displaying a high anticoagulant activity.

This application describes a series of such new low molecular weight compounds displaying a high anticoagulant activity, and in particular, compounds of general structural formula (I), and their pharmaceutically acceptable salts or solvates:

wherein C is chosen from a group containing the following structures:

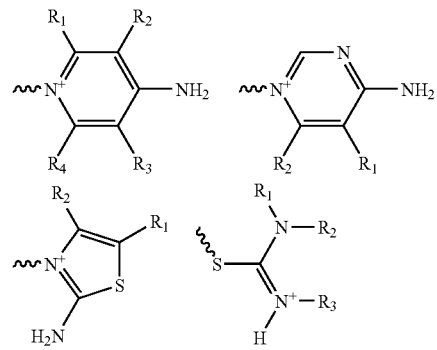

wherein $R_1$, $R_2$, $R_3$, and $R_4$ are, independently from one another, hydrogen or $C_{1-6}$ alkyl;

B—$(CH_2)_n$—, wherein n is an integer from 1 to 5; and

A is selected from a group containing the structures:

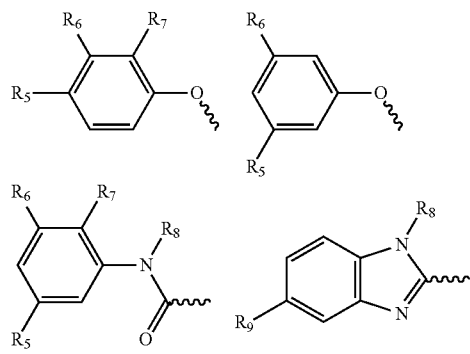

wherein $R_5$ is selected from a group containing hydrogen, $C_{1-6}$-alkoxy, $CH_2NR_{10}R_{11}$, and $CH(CH_3)NR_{10}R_{11}$,

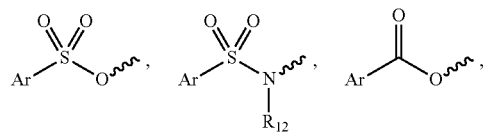

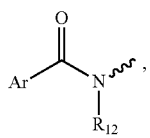

wherein $R_6$ and $R_7$ are, independently from each other, hydrogen, $C_{1-6}$ alkyl; $C_{1-6}$ alkoxy; or halogen;

$R_8$ is hydrogen or $C_{1-6}$ alkyl;

$R_9$ is chosen from the following group consisting of:

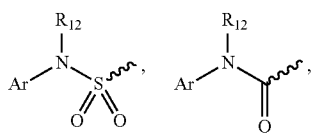

$R_{10}$ and $R_{12}$ are, independently from each other, selected from a group consisting of hydrogen, $C_{1-6}$ alkyl; $(CH_2)_m COOR_{13}$, and $(CH_2)_m CON(R_{13})_2$,

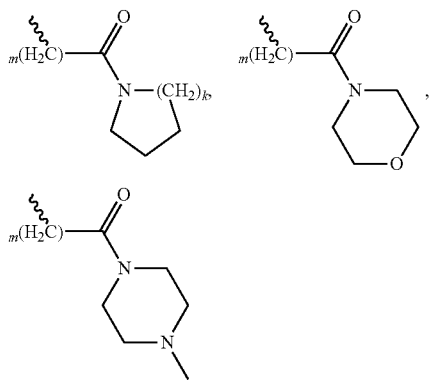

wherein m is an integer from 1 to 4, $R_{13}$ is hydrogen or $C_{1-6}$ alkyl, $R_{11}$ is $C_{1-6}$ alkyl or Ar;

Ar is phenyl, pyridyl, oxazolyl, thiazolyl, thienyl, furanyl, pyrimidinyl, pyridazinyl, pyrazinyl, indolyl, benzofuranyl, or benzothiophenyl having from one to five substituents selected from the group of:

hydrogen, $C_{1-6}$ alkyl, $C_{1-6}$ alkoxy, halogen, $N(R_{13})_2$, OH, $NO_2$, CN, $COOR_{13}$, $CON(R_{13})_2$, and $SO_2 R_{13}$;

with the exception of:

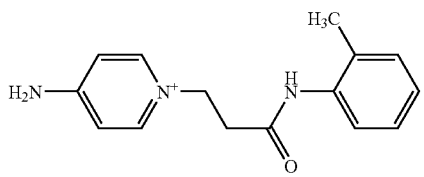

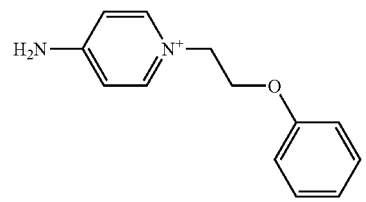

The compounds excluded from this list are already known, in particular, 4-amino-1-[3-[(2-methylphenyl)amino]-3-oxo-propyl]pyridinium chloride is described in the *Journal of Medicinal Chemistry*, 17(7), 739-744, 1974, in "Carbocyclic Derivatives Related to Indoramin;" 4-amino-1-(2-phenoxy-ethyl)-pyridinium bromide is described in the *Journal of Organic Chemistry*, 26, 2740-7, 1961, in "Application of Sodium Borohydride Reduction to Synthesis of Substituted Aminopiperidines, Aminopiperazines, Aminopyridines, and Hydrazines." It is worthwhile to note, though, that these sources do not refer to the possibility of the compounds described being used as thrombin inhibitors.

The preferred embodiment of this invention describes the following compounds of claim 1, and their pharmaceutically acceptable salts or solvates:

a)

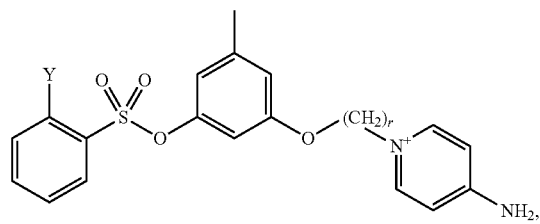

b)

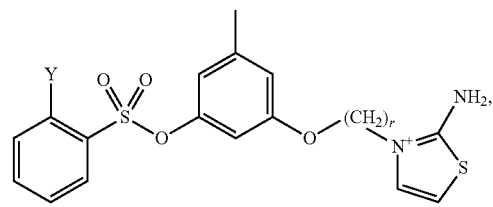

c)

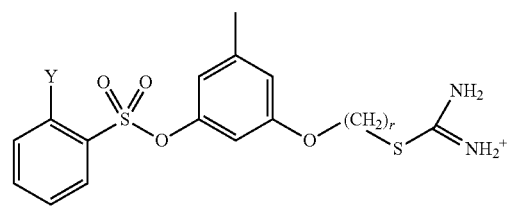

wherein Y is chosen from a group consisting of hydrogen, halogen, $COOR_{13}$, $CON(R_{13})_2$, and $SO_2R_{13}$; and r is an integer from 2 to 5.

This application also describes administration of a compound of formula (I) and its pharmacologically acceptable salts and solvates as anticoagulants for treating and preventing various thrombotic conditions, and a pharmaceutical composition for treating thrombotic conditions, containing a therapeutically effective quantity of a compound as claimed in claim 1, and/or its pharmaceutically acceptable salts and/or solvates, and a pharmaceutically acceptable carrier.

This application describes a novel plasma-substituting solution (PSS) containing a compound of formula (I) and its pharmacologically acceptable salts or solvates as an anticoagulant. This solution is prepared by adding a compound of formula (I) and its pharmacologically acceptable salts or solvates to standard plasma-substituting solutions. The concentration of the anticoagulant added depends on its inhibiting power and can vary within a wide range (from 0.01 nM to 1 mM) for different compounds. An anticoagulant-containing solution can, in part, correct the hypercoagulation disorders developing in the organism in consequence of massive transfusions of standard plasma-substituting solutions that do not contain clotting factors and, even more important, clotting inhibitors. The novel PSS containing an artificial, synthetic low molecular weight anticoagulant is advantageously superior to a similar solution containing the natural thrombin inhibitor ATIII, because it contains a less expensive, standard inhibitor in place of the expensive natural protein (ATIII) and poses no threat of viral infection during PSS infusion.

The compounds of this invention can be administered in any suitable manner leading to their bioaccumulation in blood. This can be achieved by parenteral administration methods, including intravenous, intramuscular, intracutaneous, subcutaneous, and intraperitoneal injections. Other administration methods can be used as well, such as absorption through the gastrointestinal tract by peroral application of appropriate compositions. Peroral application is preferred because of easy use. Alternatively, the medication can be administered through the vaginal and rectal muscle tissue. In addition, the compounds of this invention can be injected through the skin (for example, transdermally) or administered by inhalation. Understandably, the preferred method of administration depends on the condition, age, and susceptibility of the patient.

For peroral application, pharmaceutical compositions can be packaged, for example, into tablets or capsules together with pharmaceutically acceptable additives, such as binding agents (for example, peptized maize starch, polyvinyl pyrrolidinone or hydroxypropyl methylcellulose). Fillers (for example, lactose, microcrystalline cellulose, calcium hydrophosphate; magnesium stearate, talk or silicon oxide; potato starch or starchy sodium glycolate); or wetting agents (for example, sodium laurylsulfate). Tablets may be coated. Liquid oral compositions can be prepared in the form of, for example, solutions, syrups or suspensions. Such liquid compositions can be obtained by common methods using pharmaceutically acceptable additives, such as suspending agents (for example, cellulose derivatives); emulsifiers (for example, lecithin), diluents (purified vegetable oils); and preservatives (for example, methyl or propyl-n-hydroxybenzoates or sorbic acid). The compositions may also contain appropriate buffering salts, flavoring agents, pigments, and sweeteners.

The toxicity of these thrombin inhibitors was measured using standard pharmaceutical procedures on experimental animals to measure $LD_{50}$ (a lethal dose for 50% of the population). For preferred compounds of this invention, the $LD_{50}$ dose was in excess of 367 mg/kg, which is consistent with the lethal dose of Argatroban after clinical testing, having $LD_{50}$=475 mg/kg.

For the subject matter of this invention to be more comprehensible, following below are several examples illustrating the production of new compounds and methods that were used to study the anticoagulant activity of these compounds and the results of the studies. The examples are only illustrations, and the idea of this invention is in no way limited to the scope of the examples given below.

EXAMPLE 1

Synthesis of an intermediate product of 3-(3-chloropropoxy)-5-methylphenol

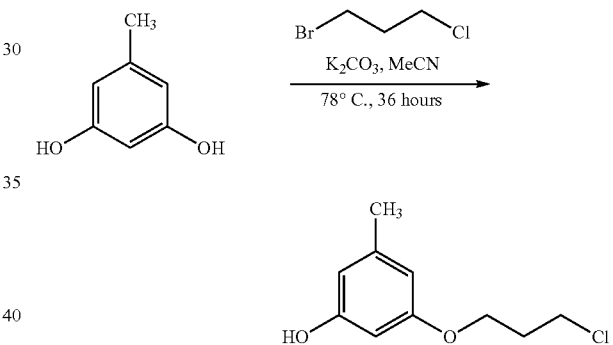

A mixture of 3.8 g (27 mmol) of orcin hydrate, 4.8 g (30 mmol) of 1-bromo-3-chloropropane, and 4.0 g (29 mmol) of potassium carbonate was boiled in 30 ml of acetonitrile at stirring for 36 hours. The reaction mixture was then evaporated, dissolved in 30 ml of ether, washed twice by 15 ml of a saturated solution of potassium carbonate, the water layer was discarded, and the ether layer was extracted 3 times by 15 ml of 10% solution of sodium hydroxide. The ether layer was discarded, the water layer was carefully acidified with concentrated HCl, and then extracted with 3 by 15 ml of ether. The ether extracts were combined, washed with small quantities of a saturated solution of sodium hydrocarbonate, and dried with anhydrous sodium sulfate, diluted with approximately ⅓rd part (by volume) of hexane, and filtered through a layer of silica gel. Evaporation yielded 1.7 g of yellow oil, a mixture of about 70% orcin (Rf 0.10) and about 30% 3-(2-chloropropoxy)-5-methylphenol (Rf 0.26, yield about 1.2 g (22% per pure substance)).

A similar method was used to produce 3-(2-chloroethoxy)-5-methylphenol (Rf 0.26, yield about 1.1 g (20% per pure substance)) from orcin hydrate and 1-bromo-2-chloroethane, and 3-(4-chlorobutoxy)-5-methyl phenol was obtained from orcin hydrate and 1-bromo-4-chorobutane.

EXAMPLE 2

Synthesis of an intermediate product of 3-(3-chloropropoxy)-5-methylphenyl ester of 2-fluorobenzene sulfonic acid

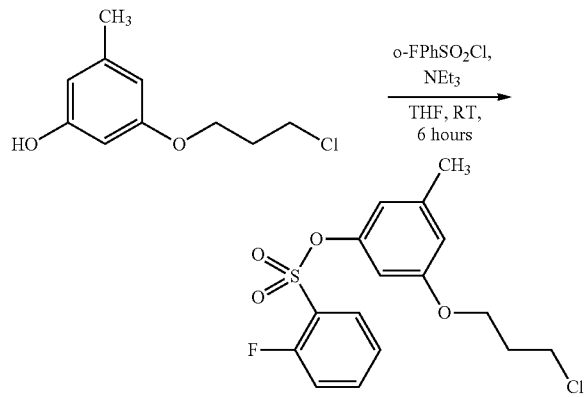

2.05 g (10 mmol) of fluorobenzene sulfochloride and 1.1 g (11 mmol) of triethylamine were added to a solution of 1.3 g of the mixture of Example 1A in 30 ml of dry tetrahydrofuran (THF). The mixture was stirred for 6 hours, the precipitate of triethylammonium hydrochloride was filtered off and evaporated. The resultant oil was dissolved in 20 ml of ether and washed several times in 10 ml of about 10-12% aqueous solution of ammonia to separate excess unreacted benzene sulfochloride (control by thin-layer chromatography (TLC)) and then 10 ml of approximately 20% hydrochloric acid. Drying with anhydrous sodium sulfate and evaporation gave 2.4 g of light-yellow oil that was a mixture of the target product and dibenzene-sulfonylated orcin at a ratio of approximately 2:1, yield in terms of pure target product was 1.6 g (97% from reaction) (TLC of Merck plate 60, hexane-ethylacetate 2:1. Rf 0.35—product, Rf 0.25—dibenzene ester impurity).

Similarly, 3-(2-chloroethoxy)-5-methylphenol, 3-(3-chloropropoxy)-5-methylphenol, and 3-(4-chlorobutoxy)-5-methylphenol and appropriate arylsulfochlorides gave:

3-(3-chloropropoxy)-5-methylphenyl ester of 2-chlorobenzene sulfonic acid (77% per pure substance).

3-(3-chloropropoxy)-5-methylphenyl ester of benzene sulfonic acid (60%).

3-(3-chloropropoxy)-5-methylphenyl ester of 2-carbomethoxy benzene sulfonic acid (56%).

3-(2-chloroethoxy)-5-methylphenyl ester of benzene sulfonic acid (72%).

3-(2-chloroethoxy)-5-methylphenyl ester of 2-chlorobenzene sulfonic acid (35%).

3-(2-chloroethoxy)-5-methylphenyl ester of 2-fluorobenzene sulfonic acid (34%).

3-(2-chloroethoxy)-5-methylphenyl ester of 2-carbomethoxy benzene sulfonic acid (37%).

3-(4-chlorobutoxy)-5-methylphenyl ester of benzene sulfonic acid (45%).

3-(4-chlorobutoxy)-5-methylphenyl ester of 2-chlorobenzene sulfonic acid (27%).

3-(4-chlorobutoxy)-5-methylphenyl ester of 2-fluorobenzene sulfonic acid (32%).

3-(4-chlorobutoxy)-5-methylphenyl ester of 2-carbomethoxy benzene sulfonic acid (21%).

EXAMPLE 3

Synthesis of an intermediate product of 3-(3-iodopropoxy)-5-methylphenyl ester of 2-fluorobenzene sulfonic acid

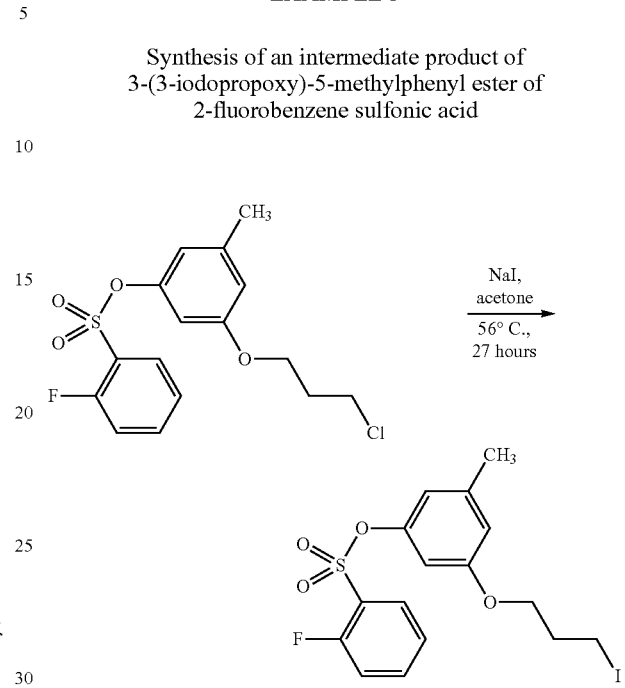

hereinafter, for briefness FPhO-3-I 2 g (13 mmol) of calcined sodium iodide was added to 2.4 g of the mixture of the preceding experiment (2A) in 30 ml of dry acetone and boiled for 27 hours. The reaction mixture was then diluted with 10 ml of hexane, filtered and evaporated. The resultant dark-yellow oil was dissolved in 20 ml of an ether-hexane mixture (2.3 g), filtered through a silica gel layer (2 cm, Lancaster), and evaporated. The result was 2.45 g of yellow oil containing 3-(2-iodoethoxy)-5-methylphenyl ester of 2-fluorobenzene sulfonic acid (Rf 0.35) and a respective dibenzoyl sulfonic ester of orcin (Rf 0.25).

A similar technique was used to process the appropriate chlorides into:

3-(3-iodopropoxy)-5-methylphenyl ester of benzene sulfonic acid 3-(3-iodopropoxy)-5-methylphenyl ester of 2-chlorobenzene sulfonic acid 3-(3-iodopropoxy)-5-methylphenyl ester of 2-carbomethoxy benzene sulfonic acid 3-(2-iodoethoxy)-5-methylphenyl ester of benzene sulfonic acid 3-(2-iodoethoxy)-5-methylphenyl ester of 2-chlorobenzene sulfonic acid 3-(2-iodoethoxy)-5-methylphenyl ester of 2-fluorobenzene sulfonic acid 3-(2-iodoethoxy)-5-methylphenyl ester of 2-carbomethoxy benzene sulfonic acid 3-(4-iodobutoxy)-5-methylphenyl ester of benzene sulfonic acid 3-(4-iodobutoxy)-5-methylphenyl ester of 2-chlorobenzene sulfonic acid 3-(4-iodobutoxy)-5-methylphenyl ester of 2-fluorobenzene sulfonic acid 3-(4-iodobutoxy)-5-methylphenyl ester of 2-carbomethoxy benzene sulfonic acid

EXAMPLE 4

Synthesis of 4-amino-1-(3-(3-methyl-5-(2-fluorobenzene sulfonyloxy)phenoxy)propyl)-pyridinium iodide (HC_029s_IOC)

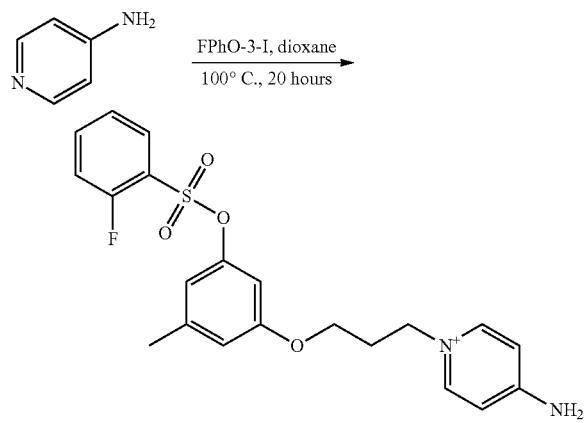

A mixture of 0.65 g of "raw iodide" (from Experiment 3A) (calculated for 70% of active substance) and 0.09 g (0.95 mmol) of 4-aminopyridine in 10 ml of dry dioxane was boiled for 20 hours. After the mixture cooled off, the solution was evaporated, and the resultant oil was ground with a few portions of ether until it turned solid. The solid precipitate was filtered off and recrystallized from a mixture of dioxane and acetonitrile (5:1), the salt precipitate was filtered off, and washed with ether. Drying in vacuum yielded 0.4 g (72%) of light-beige salt containing about 4-5% of unidentified impurities. The substance was again recrystallized from the same system to remove the impurities, giving 0.25 g of light-colored powder.

A similar technique was used to process appropriate iodides and heterocyclic compounds, thiourea, and thiourea derivatives into:

4-amino-1-(3-(3-methyl-5-(benzene sulfonyloxy)phenoxy)propyl)-pyridinium iodide (HC_016s_IOC)

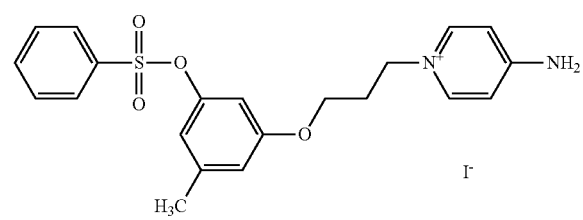 [SMILES: Cc1cc(OCCC[n+]2ccc(N)cc2)cc(OS(=O)(=O)c2ccccc2)c1 ; [I-]]

Yield 78%.

NMR $^1$H (Bruker DRX500, 500 MHz, DMSO-d6, m.d., J Hz): 2.20 s, 3H; 3.88 t, 2H, J=5.50; 2.16 m, 2H, J=6.11; 4.25 t, 2H, J=6.71; 6.31 s, 1H, 6.44 s, 1H, 6.66 s, 1H; 7.68 t, 2H, J=7.94, 7.82 t, 1H, J=7.94, 7.87 d, 2H, J=7.32; 6.81 d, 2H, J=6.72, 8.17 d, 2H, J=6.72; 8.09 s, 2H 2-amino-1-(3-(3-methyl-5-(benzene sulfonyloxy)phenoxy)propyl)-thiazolium iodide (HC_017s_IOC)

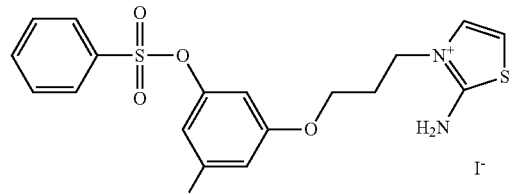

Yield 65%.

NMR $^1$H (Bruker DRX500, 500 MHz, DMSO-d6, m.d., J Hz): 2.21 s, 3H; 3.93 t, 2H, 7=6.11; 2.11 m, 2H, J=6.10; 4.15 t, 2H, J=6.71; 6.35 s, 1H, 6.44 s, 1H, 6.68 s, 1H, 7.69 t, 2H, J=7.33, 7.84 t, 1H, J=7.32, 7.88 d, 2H, J=7.93; 7.02 d, 1H, J=4.27, 7.42 d, 1H, J=4.27; 9.42 s, 2H 3-(3-methyl-5-(benzene sulfonyloxy)phenoxy)propyl-isothiouronium iodide (HC_018s_IOC)

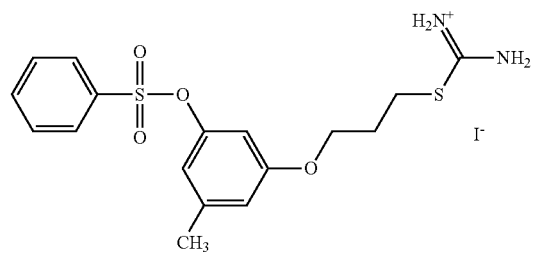 [SMILES: Cc1cc(OCCCSC(N)=[NH2+])cc(OS(=O)(=O)c2ccccc2)c1 ; [I-]]

Yield 80%.

NMR $^1$H (Bruker DRX500, 500 MHz, DMSO-d6, m.d., J Hz): 2.21 s, 3H, 3.95 t, 2H, J=6.10; 2.00 m, 2H, 1=6.71; 3.25 t, 2H, J=7.32; 6.40 s, 1H, 6.25 s, 1H, 6.74 s, 1H, 7.69 t, 2H, J=7.94, 7.84 t, 1H, J=7.93, 7.89 d, 2H, J=7.33; 9.03 s, 4H 4-amino-1-(2-(3-methyl-5-(benzene sulfonyloxy)phenoxy)ethyl)-pyridinium iodide (HC_019s_IOC)

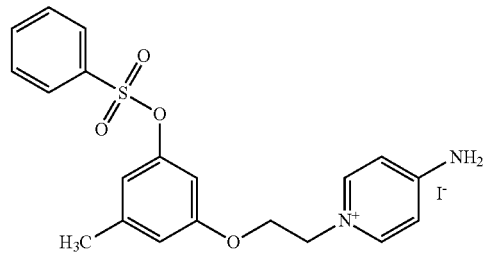 [SMILES: Cc1cc(OCC[n+]2ccc(N)cc2)cc(OS(=O)(=O)c2ccccc2)c1 ; [I-]]

Yield 60%.

NMR $^1$H (Bruker DRX500, 500 MHz, DMSO-d6, m.d., J Hz): 2.20 s, 3H, 4.24 t, 2H, J=4.88; 4.48 t, 2H, J=4.89; 6.39 s, 1H, 6.45 s, 1H, 6.73 s, 1H, 7.68 t, 2H, 3=7.93, 7.82 t, 1H, 3=7.93, 7.87 d, 2H, J=7.32; 6.82 d, 2H, J=7.32, 8.18 d, 2H, 1=7.33; 8.14 s, 2H 2-(3-methyl-5-(benzene sulfonyloxy)phenoxy)ethyl-isothiouronium iodide (HC_020s_IOC)

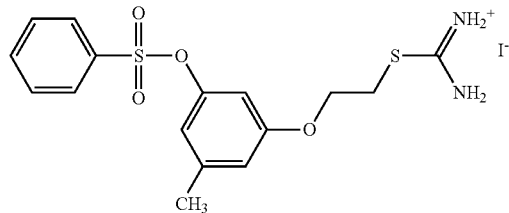

Yield 45%.
NMR ¹H (Bruker DRX500, 500 MHz, DMSO-d6, m.d., J Hz): 2.22 s, 3H, 4.11 t, 2H, 3=5.49; 3.54 t, 2H, J=5.49; 6.41 s, 1H, 6.48 s, 1H, 6.76 s, 1H, 7.69 t, 2H, J=7.93, 7.84 t, 1H, J=7.93, 7.89 d, 2H, 1=7.32; 9.10 s, 4H 2-(3-methyl-5-(2-chlorobenzene sulfonyloxy)phenoxy)ethyl-isothiouronium iodide (HC_024s_IOC)

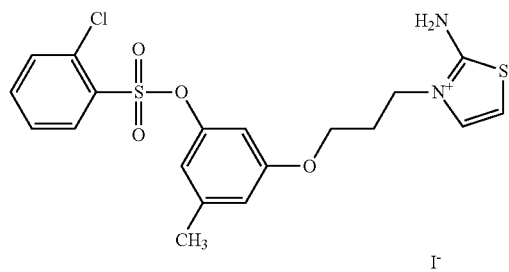 [SMILES: Cc1cc(OCCC[n+]2ccsc2N)cc(OS(=O)(=O)c2ccccc2Cl)c1 ; [I-]]

Yield 53%.
NMR ¹H (Bruker DRX500, 500 MHz, DMSO-d6, m.d., J Hz): 2.21 s, 3H; 3.95 t, 2H, 3=5.50; 2.12 m, 2H, 3=5.50; 4.15 t, 2H, 3=6.10; 6.42 t, 1H, 6.51 s, 1H, 6.70 s, 1H, 7.59 t, 1H, 7=7.32, 7.83 t, 1H, J=7.94, 7.88 d, 1H, J=7.94, 7.95 d, 1H, J=7.94; 7.01 d, 1H, J=4.27, 7.42 d, 1H, J=4.27; 9.39 s, 2H 3-(3-methyl-5-(2-chlorobenzene sulfonyloxy)phenoxy)propyl-isothiouronium iodide (HC_026s_IOC)

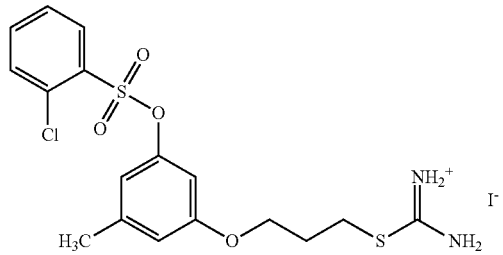 [SMILES: Cc1cc(OCCCSC(N)=[NH2+])cc(OS(=O)(=O)c2ccccc2Cl)c1 ; [I-]]

Yield 55%.
NMR ¹H (Bruker DRX500, 500 MHz, DMSO-d6, m.d., J Hz): 2.22 s, 3H; 3.97 t, 2H, J=6.10; 2.01 m, 2H, J=7.33, J=6.10; 4.26 t, 2H, J=7.33; 6.47 s, 1H, 6.51 s, 1H, 6.75 s, 1H, 7.60 t, 1H, J=7.93, 7.84 t, 1H, J=7.94, 7.88 d, 1H, J=7.93, 7.96 d, 1H, J=7.94; 8.95 s, 2H, 9.07 s, 2H 4-amino-1-(2-(3-methyl-5-(2-chlorobenzene sulfonyloxy)phenoxy)ethyl)-pyridinium iodide (HC_025s_IOC)

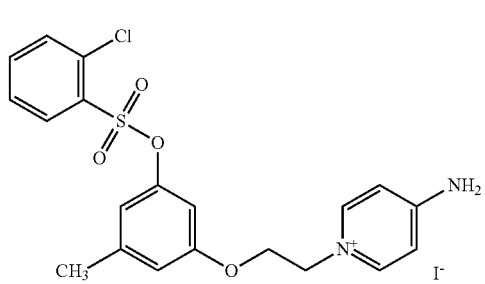 [SMILES: Cc1cc(OCC[n+]2ccc(N)cc2)cc(OS(=O)(=O)c2ccccc2Cl)c1 ; [I-]]

Yield 58%.
NMR ¹H (Bruker DRX500, 500 MHz, DMSO-d6, m.d., J Hz): 2.20 s, 3H; 4.26 t, 2H, J=4.88; 4.49 t, 2H, J=4.88; 6.45 s, 1H, 6.51 s, 1H, 6.74 s, 1H, 7.58 t, 1H, J=7.93, 7.84 t, 1H, J=7.94, 7.88 d, 1H, J=7.93, 7.94 d, 1H, J=7.94; 6.82 d, 2H, J=7.32, 8.18 d, 2H, J=7.33; 8.14 s, 2H.

In a similar way, by techniques described in examples 1-4, compounds were synthesized from various aryl sulfonyl chlorides and heterocyclic sulfonyl chlorides. Chemical formulae, mass-spectrometric parameters, and the computed scoring functions of the synthesized compounds are presented in Table 1. The compounds could be obtained in the form of iodides, bromides, chlorides, or other salts.

EXAMPLE 5

Synthesis of the Compounds

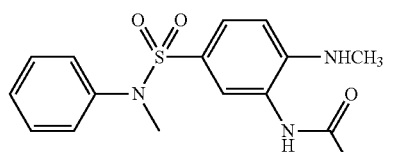

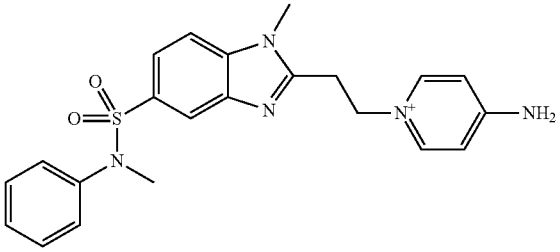

1. 4-Chloro-3-nitrobenzene-1-sulfonyl chloride o-Nitrochloroaniline (15 g) was added into 30 ml of chlorosulfonic acid with stirring and heated at 100° C. for 2 h, followed by 2 h at 110° C. and 5 h at 127° C. The reaction mixture was cooled to room temperature and poured into crushed ice (140 g). The precipitate was filtered; the filter cake was rinsed with ice water and dried in air. The crop was 15 g of 4 chloro-3-nitrobenzene-1 sulfonyl chloride.

2. 4-Chloro-N-methyl-3-nitro-N-phenylbenzene sulfonamide

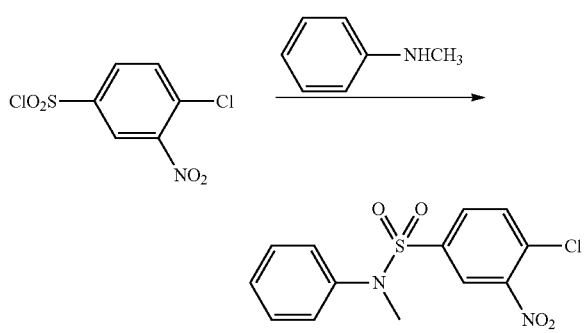

4-Chloro-3-nitrobenzene-1-sulfonyl chloride (10.6 g, 0.041 mol) was dissolved in toluene (50 ml); and triethylamine (4.14 g, 0.041 mol) was then added. To the resulting solution, N-methylaniline (4.4 g, 0.041 mol) was added under stirring. The reaction mixture was incubated at 70-80° C. for 1 h. Thereafter, it was allowed to cool. The cooled solution was washed twice with 30 ml of water and concentrated under vacuum. The residue was recrystallized from ethanol. The yield of 4-chloro-N-methyl-3-nitro-N-phenylbenzene sulfonamide was 9.4 g (61%).

3. N-methyl-4-(methylamino)-3-nitro-N-phenylbenzene sulfonamide

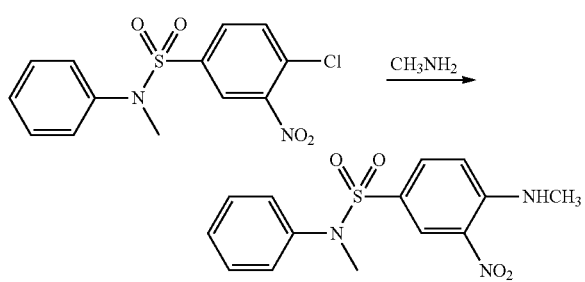

A solution of 4-chloro-N-methyl-3-nitro-N-phenylbenzoyl sulfonamide (9.4 g, 0.029 mol) in ethanol (50 ml) was combined with 25 ml of an aqueous solution of 40% methylamine. The reaction mixture was heated to 70° C. and stirred at this temperature for 1 h. After cooling and filtering, the filter cake was washed with ethanol and dried at 60° C. The yield of N-methyl-4-(methylamino)-3-nitro-N-phenylbenzoyl sulfonamide was 9.0 g (97%).

4. 3-amino-N-methyl-4-(methylamino)-N-phenylbenzene sulonamide

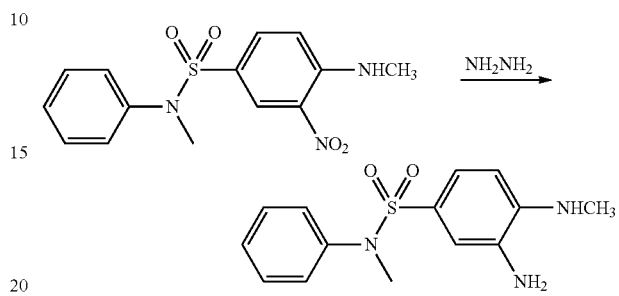

N-Methyl-4-(methylamino)-3-nitro-N-phenylbenzoyl sulfonamide (9 g, 0.028 mol) was dissolved in isopropanol (90 ml). To this solution, hydrazine hydrate (11 ml), activated charcoal (2 g), and $FeCl_3 \cdot 6H_2O$ (0.5 g in 10 ml ethanol) were added. The reaction mixture was boiled for 8 h. The charcoal was removed by filtration. The filtrate was evaporated to dryness. The yield of 3-amino-N-methyl-4-(methylamino)-N-phenylbenzene sulfonamide was 8.1 g (99%).

5. 3-chloro-N-(5-(N-methyl-N-phenyl sulfamoyl)-2-(methylamino)phenyl)propanamide

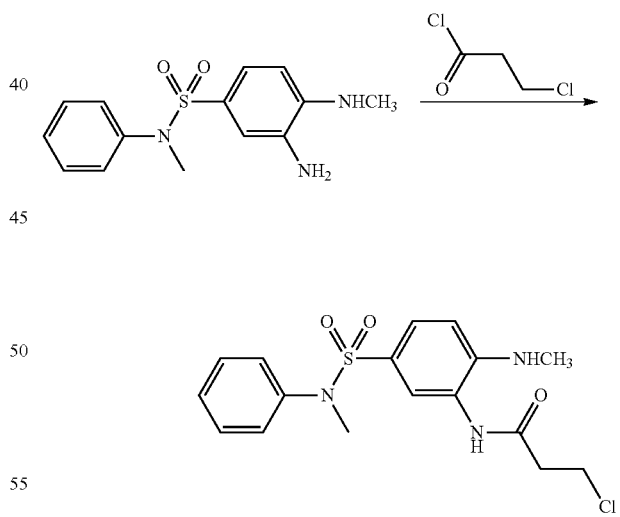

To a solution of 3-amino-N-methyl-4-(methylamino)-N-phenylbenzene sulfonamide (5.4 g, 0.018 mol) and triethylamine (1.81 g, 0.018 mol) in dimethylformamide (16 ml) being cooled on ice (~5° C.), chloropropionyl chloride (2.32 g, 0.018 mol) was added. The reaction was stirred at room temperature for 5 h. Thereupon, water (14 ml) and acetonitrile (5 ml) were added for 5 h. The precipitate formed was filtered. The yield of 3-chloro-N-(5-(N-methyl-N-phenylsulfamoyl)-2-(methylamino)phenyl)propanamide was 3.1 g (45%).

6. 4-amino-1-(3-(5-(N-methyl-N-phenylsulfamoyl)-2-(methylamino)phenylamino)-3-oxopropyl)pyridinium chloride

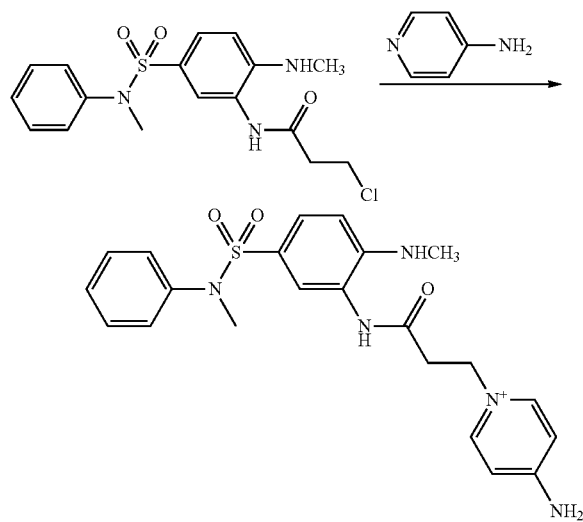

3-Chloro-N-(5-(N-methyl-N-phenylsulfamoyl)-2-(methylamino)phenyl)propanamide (1 g, 0.0026 mol) and 4-aminopyridinium (0.73 g, 0.0078 mol) were boiled in anhydrous acetone (50 ml) for 50 h. The residue was filtered and subjected to crystallization from a 10:1 mixture of acetonitrile with ethanol.

The Yield of 4-amino-1-(3-(5-(N-methyl-N-phenylsulfamoyl)-2-(methylamino)phenylamino)-3-oxopropyl)pyridinium chloride was 0.54 g (43%).

7. 4-amino-1-(2-(1-methyl-5-(N-methyl-N-phenylsulfamoyl)-1H-benzo[d]imidazol-2-yl)ethyl)pyridinium chloride

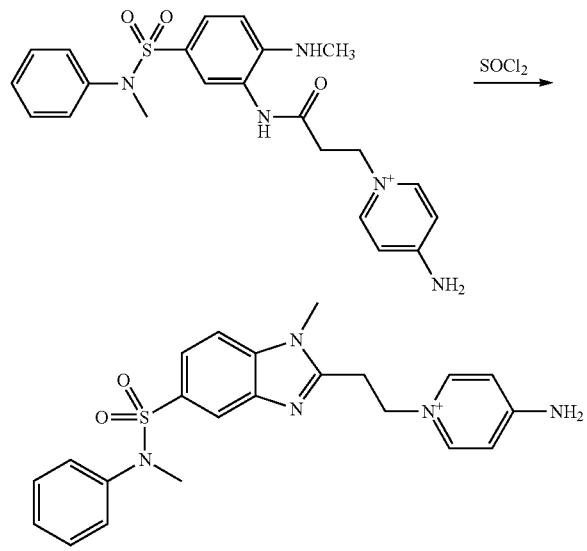

To a suspension of 4-amino-1-(3-(5-(N-methyl-N-phenylsulfamoyl)-2-(methylamino)phenylamino)-3-oxopropyl)pyridinium chloride (0.2 g, 0.00042 mol) in acetonitrile (8 ml), thionyl chloride (0.2 ml) was added. After boiling the reaction mixture for 10 min, it was left to stand at room temperature for 24 h and then diluted with diethyl ether (8 ml). The precipitate formed was collected by filtration and crystallized from a 10:1 mixture of acetonitrile with dehydrated ethanol. The yield of 4-amino-1-(2-(1-methyl-5-(N-methyl-N-phenylsulfamoyl)-1H-benzo[d]imidazol-2-yl)ethyl)pyridinium chloride was 0.055 g (26%).

In a similar way, by techniques described in example 5, various compounds were synthesized, for which chemical formulae, mass-spectrometric parameters, and the computed scoring functions are presented in Table 2. The compounds could be obtained in the form of iodides, bromides, chlorides, or other salts.

EXAMPLE 6

Assessment of the Effect of Synthesized Compounds on Hemostasis

The status of the clotting system in the presence of newly synthesized compounds was assessed in this study using a standard clotting test to measure thrombin clotting time (TT) and two modern in vitro tests—thrombin generation and measurement of the clot growth rate in space. As distinct from the standard tests to measure clotting time, which were conducted against the background of maximum clotting activation on the internal or external path, respectively, and, for this reason, cannot detect the hypercoagulation condition in the system studied, these tests were carried out at a considerably lower initial activation, close to that existing in the organism. This makes them sensitive to both hypo- and hypercoagulation in the plasma samples studied.

Thrombin Time Measurement

The thrombin clotting time test is the last in the series of clotting reactions, that is, conversion of plasma fibrinogen into an insoluble fibrin clot under the effect of thrombin added to the system. A fixed quantity of thrombin at standard activation level was added to platelet-poor plasma (PPP), which was obtained by centrifuging (15 minutes at 1,300 g) blood prepared on 3.8% sodium citrate (at pH=5.5) (blood to citrate ratio=9:1). The clotting time measured in this test depended on the number of thrombin inhibitors present in the blood. It grew when a strong thrombin inhibitor was present in the system, reducing the activity of the enzyme added and, in this way, delaying clotting.

Thrombin time was measured by standard methodologies (Z. S. Barkagan, A. P. Momot, "Diagnostics and Controlled Therapy of Hemostatic Disorders," Newdiamed, Moscow, 2001, pp. 87-89). In particular, 90 microliters of PPP heated on a water bath at 37° C. for 3 minutes was placed in the cuvette of an aggregometer from Biola Ltd., Russia, followed by addition of 10 microliters of a mixture of the test substance and a buffer (to achieve an end concentration varying from 0.005 mM to 5 mM for different compounds in the cuvette) and 100 microliters of thrombin solution (standardized according to activity on normal plasma control). The clotting time was measured, and the results were averaged from three independent experiments.

Measurement of Endogenous Thrombin Potential (Thrombin Generation Test)

This method was described in detail in many papers (Hemker H C, Giesen P L, Ramjee M, Wagenvoord R, Beguin S. The thrombogram: monitoring thrombin generation in platelet-rich plasma. Thromb. Haemost., 2000; 83(4): 589-591; Hemker H C, AlDieri R, Beguin S. Thrombin generation assays: accruing clinical relevance. Curr. Opin. Hematol., 2004, 11(3):170-175; Hemker H C, Giesen P, AlDieri R, Regnault V, de Smed E, Wagenvoord R, Lecompte T, Beguin S. The calibrated automated thrombogram (CAT): a universal routine test for hyper- and hypocoagulability. Pathophysiol. Haemost. Thromb., 2002, 32(5-6):249-253). The test is used to measure the kinetics and total quantity of active thrombin generated in a plasma sample over a specified time at a standard clotting activation level in the sample. These applicants' method is suitable for measuring thrombin concentration using a slow-action fluorogenic substrate (BOC-Ile-Gly-Arg-AMC), which gives a highly fluorescent product, 7-amino-4-methylcoumarin (AMC), when broken d own by thrombin. The use of a fluorogenic, rather than chromogenic, substrate is dictated by the fact that the fluorescence level in the sample is virtually unaffected by the solid fibrin clot formed in the metering cell, but this is a qualification that restricts the application of a chromogenic substrate (Hemker H C, Giesen P, AlDieri R, Regnault V, de Smed E, Wagenvoord R, Lecompte T, Beguin S. The calibrated automated thrombogram (CAT): a universal routine test for hyper- and hypocoagulability. Pathophysiol. Haemost. Thromb., 2002, 32(5-6):249-253). On the other hand, it is common knowledge that the bulk of thrombin (about 95%) in the sample is generated after the first clot has already formed (Hemker H C, AlDieri R, Beguin S. Thrombin generation assays: accruing clinical relevance. Curr. Opin. Hematol., 2004, 11(3):170-175).

The kinetics of thrombin generation and ultimately loss in plasma after clotting activation is shown in FIG. 1, which illustrates the relationship between concentration of active thrombin in a plasma sample and time. The area under the thrombin generation time curve (in this invention, from 0 to 50 minutes of incubation) is called endogenous thrombin potential (ETP). The curve is further characterized by $t_{max}$, the time when thrombin in the sample reaches maximum concentration, $A_{max}$, the maximum thrombin concentration in the system, and $t_{lag}$, the time before clotting commencement, which is conventionally the time when thrombin reaches a concentration of 5 nM.

Obviously, important clotting information is contained in the shape of thrombin concentration to time curves, as well as the integral ETP level. In particular, against the background of low factor and clotting inhibitor concentration, thrombin concentration maximums can be lower and also broader, although the total ETP might not change at all. The presence of additional thrombin inhibitors in plasma must reduce ETP and maximum attainable thrombin concentration, and increase the clotting lag and the time required for thrombin to achieve maximum concentration.

Measurements were taken as follows: 90 microliters of normal donor plasma (PPP), 0 to 20 microliters of the test substance solution, and 20 to 0 microliters of buffering solution (20 mM of HEPES, 140 mM of NaCal, pH 7.5) were deposited in the holes of a 96 hole board so that the total volume of added substance and buffer is always 20 microliters. Whereupon 20 microliters of a fluorogenic substrate solution (at 5 mM initial concentration) was added to each of the board holes, and plasma was heated for 3 to 5 minutes at 37° C. Next, 25 microliters of a clotting activator solution was added simultaneously (using a multichannel pipette) to all the holes. A thromboplastin solution prepared from a standard thromboplastin reagent diluted to ½₅₀th of its original concentration by the same buffer further containing 80 mM of CaCl₂ to measure the prothrombin time (PT) (RENAM, Russia) was used as activator. The time when the activator was added was the start of countdown time. The kinetics of fluorescent reaction product accumulation (AMC) was recorded for 60 minutes. The product accumulation time at each point of time is proportional to the thrombin concentration present in plasma at that point. By differentiating the AMC accumulation curve, it is possible to measure the ratio of thrombin concentration in the system to time and, in consequence, measure the parameters characterizing the curve. The conventional fluorescent units were translated for each sample into absolute AMC concentrations by calibrating the signal according to signals of known AMC concentrations in these plasma samples. The linearity of the method was tested in advance within a wide range of AMC concentrations.

Measurement of the Clot Growth Rate in Space

The clot growth rate in space describes the dynamics of clotting, which is a process that develops over time and across space. This method measures light scattering to determine the size of the clot at different periods of time once clotting has begun. Clotting is activated in the system by an activator precisely localized in space without stirring. The activator was alternatively either a simple glass plate having a ground edge to cause contact activation on the internal path or fibroblast-coated polyethylene terephthalate films provided on the surface with a tissue factor to activate clotting on the external path. Where clotting was activated on the external path, a maize trypsin inhibitor was added to the initial plasma at a concentration of 200 mkg/ml to prevent contact clotting activation in the system. Measurements were made in platelet-free plasma (PFP), which was obtained by additional PPP centrifuging at 10,000 g for 10 minutes.

A micro-camera was mounted in a 35 mm polystyrene Petri dish. When clotting was activated on the external path, the end of the glass plate 1 mm thick was wrapped with a polyethylene terephthalate film on which fibroblasts had been grown. The plate was then fixed with two-sided Scotch tape at the bottom of the dish. The glass plate end served as the side edge of the micro-camera coated with an activator. Similarly, a polystyrene plate covered on the outside with black paint and extending beyond the edge of the glass plate was affixed on the top surface of the glass plate to define the top surface of the micro-camera. Recalcified platelet-free plasma (at 20 mM final concentration of added CaCl₂), with or without the prospective thrombin inhibitor was carefully poured into the spacing between the top plate and the camera bottom to avoid its contact with the clotting-activating side wall. The moment plasma came into contact with the activator was marked down as t=0. The dish was firmly sealed and placed in a thermostatic 37° C. cuvette with a transparent bottom, through which the plasma in the dish was illuminated with red diode light ($\lambda$=660 nm). The image of the permanent micro-camera area (7.2 by 5.4 mm) was registered every 30 seconds by a video camera OS-75D (Mintron Enterprise, Taiwan) connected to an image capture plate EZ98 (Lifeview Inc., USA) to be digitized and entered from the video camera into the memory of an image computer.

Light scattering profiles corresponding to different time moments from the start of the experiment were obtained by processing the series of recorded images. As it grew on, the clot was spreading further from the activator surface into the plasma. The clot size in each frame was determined as the distance from the activator to the clot edge assumed to be the point where light scattering was half the maximum value. The clot growth rate was then found as the tangent of the inclination angle of the straight line of the clot size to time. This method is described in more detail in the following papers: Ovanesov M V, Krasotkina J V, Ul'yanova L I, Abushinova K V, Plyushch O P, Domogatskii S P, Vorob'ev A I, Ataullakhanov F I. Hemophilia A and B are associated with abnormal spatial dynamics of clot growth. Biochim. Biophys. Acta, 2002, 1572(1):45-57; Ovanesov M V, Lopatina E G, Saenko E L, Ananyeva N M, Ul'yanova L I, Plyushch O P, Butilin A A, Ataullakhanov F I. Effect of factor VIII on tissue factor-initiated spatial clot growth. Thromb. Haemost., 2003, 89(2): 235-242.

Figure 2:
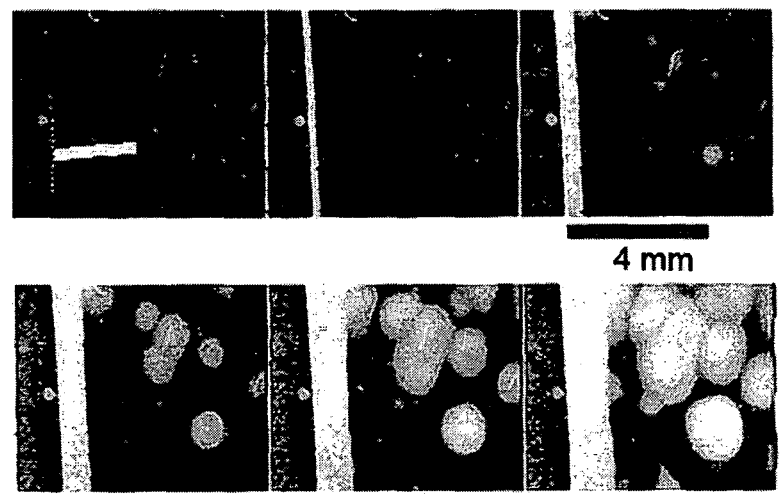
FIG. 2. Photo sequence of a clot growin in normal plasma.

FIG. 2 shows a photo sequence of a clot growing in normal plasma (the band at left is a glass activator, and fibrin is revealed by light areas). The first frame shows a band normal to the activator, on which the light scattering profiles were calculated.

Figure 3:
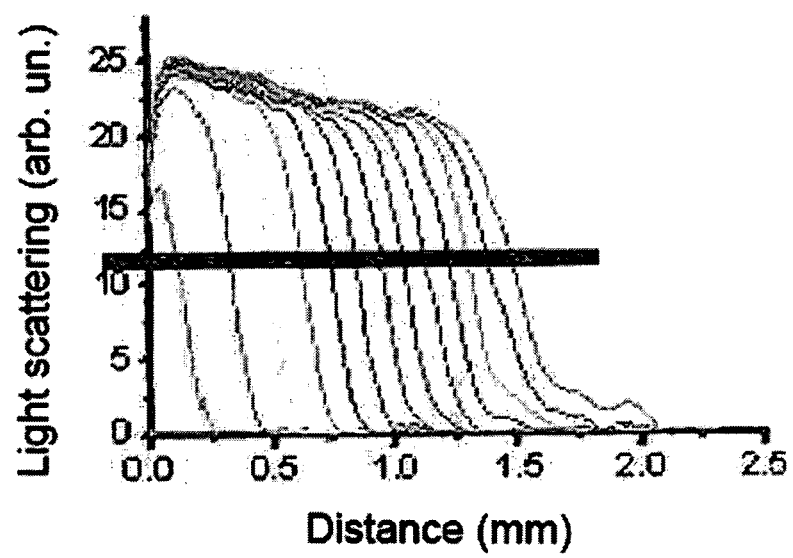
FIG. 3. Light scattering profiles of a growing clot.

The light scattering profiles of a growing clot are shown in FIG. 3 at different time points from the start of clotting.

Figure 4:
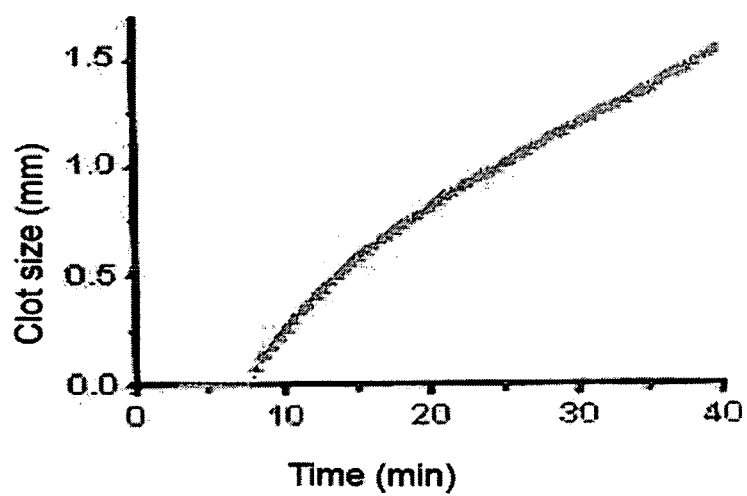
FIG. 4. Clot size as a function of time.

The last output processing stage was calculating the clot growth rate on the basis of the light scattering profiles obtained. The clot size was assessed at each point of time as the distance of a respective light scattering profile from the activator (at half-point of the maximum profile height). FIG. 4 shows the clot size to time ratio calculated. The quasi-stationary growth rate of the clot was calculated from the inclination angle of the linear portion of the curve.

The tests undertaken have shown that the newly synthesized compounds claimed in this application have anticoagulant properties, that it, they slow down plasma clotting.

Figure 5:
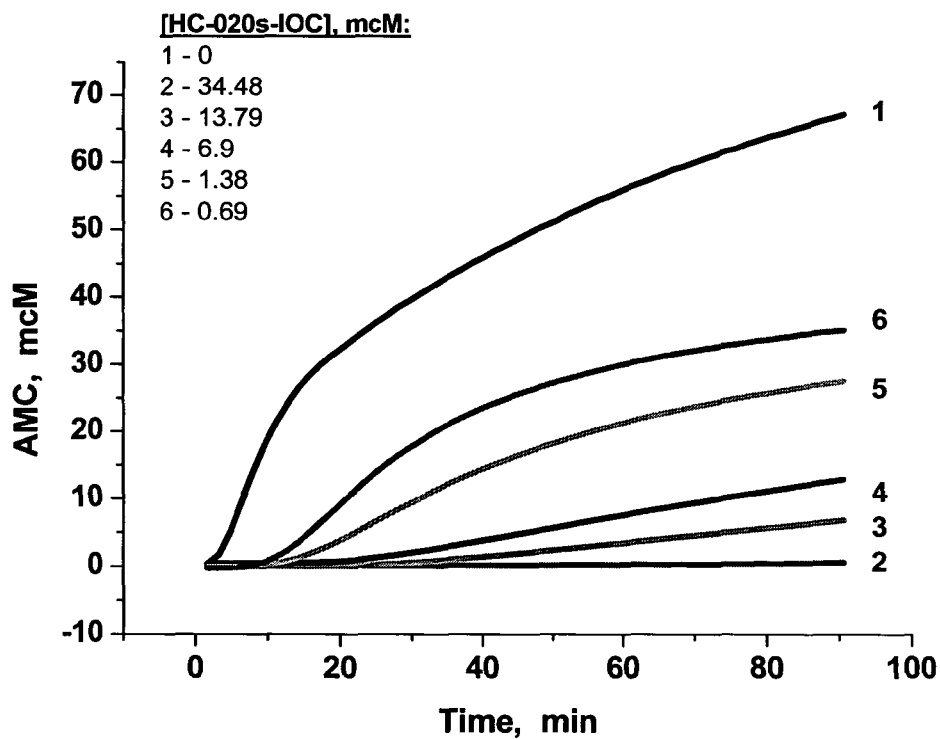
FIG. 5. Accumulation of fluorescent product in a breakdown reaction between a fluorogenic substrate and thrombin resulting from plasma clotting.
Figure 6:
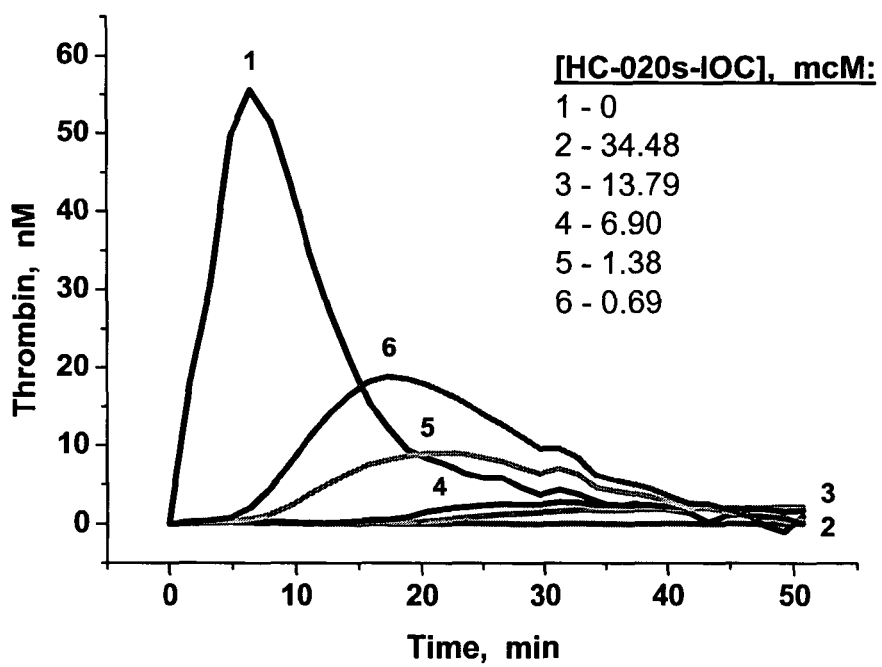
FIG. 6. Kinetic profiles of thrombin concentration changes obtained by differentiating the curves of FIG. 5.
Figure 7:
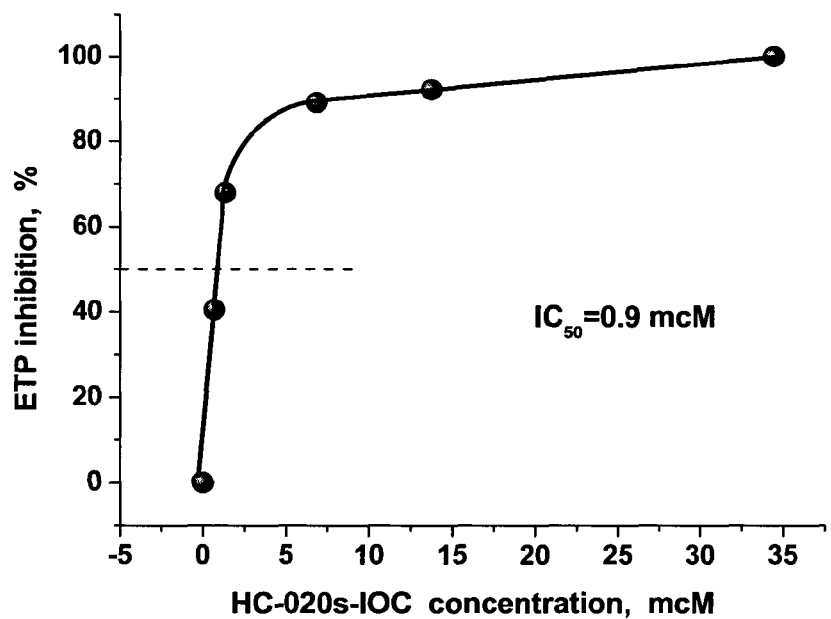
FIG. 7. Reduction in thrombin potential vs. grown in inhibitor concentration.
Figure 8:
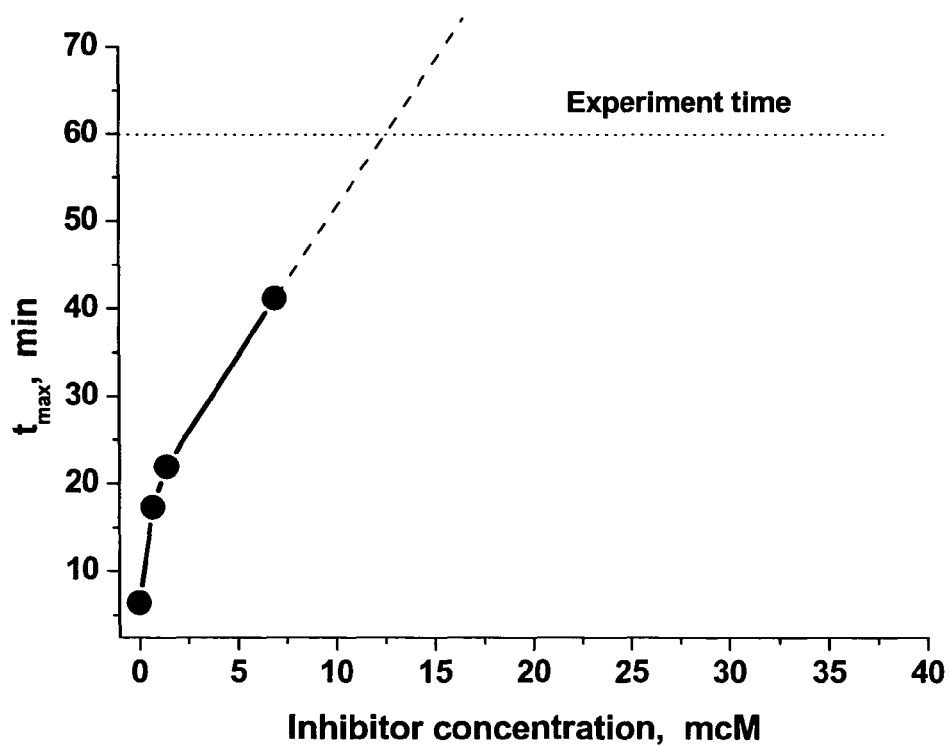
FIG. 8. Increase in time needed to reach the maximum point on the thrombin generation curve vs. growth in inhibitor concentration.
Figure 9:
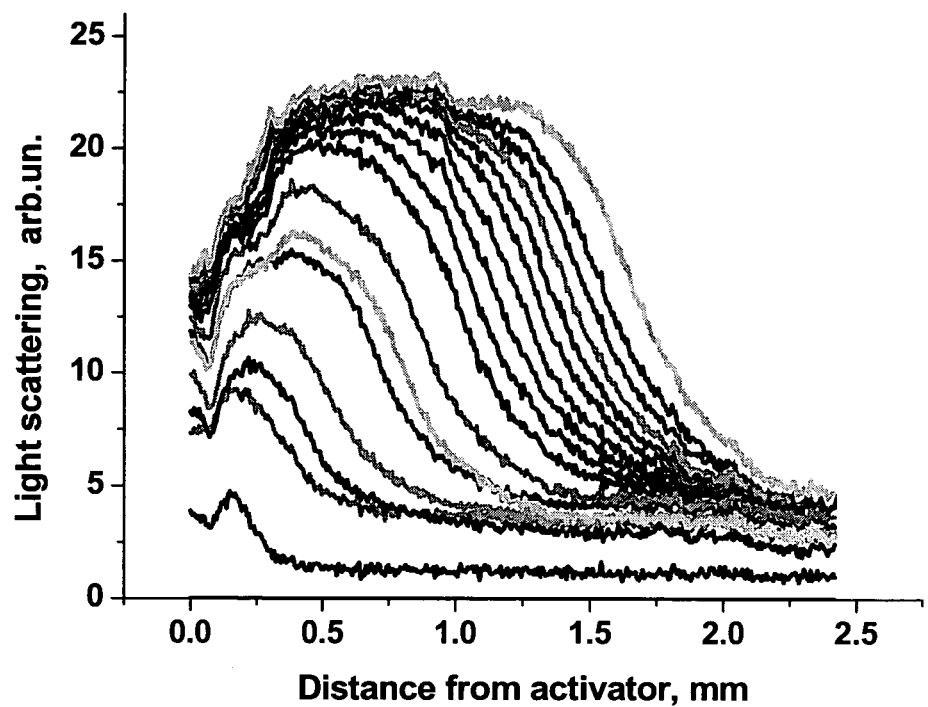
FIG. 9. Light scattering profiles registered while clotting in normal plasma.
Figure 10:
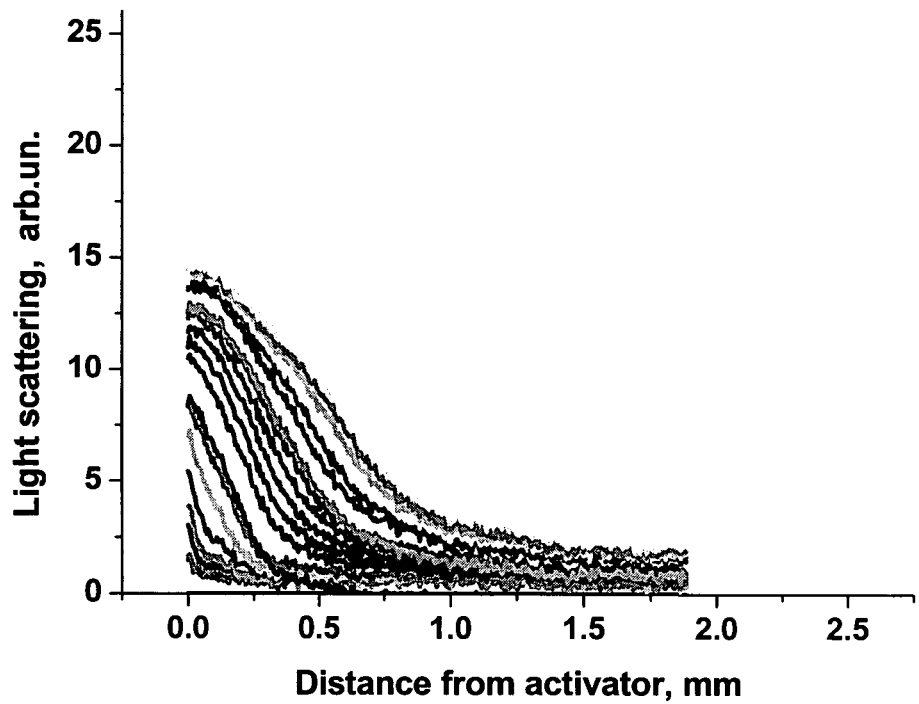
FIG. 10. Light scattering profiles registered while clotting in normal plasma in the presence of 1mcM of compound.
Figure 11:
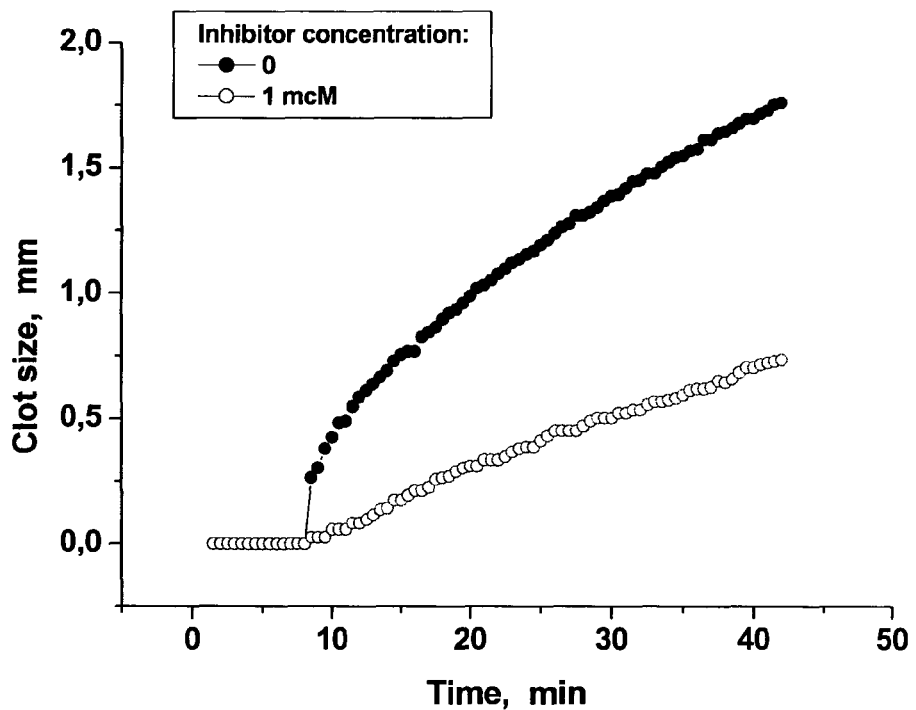
FIG. 11. Growth in clot size vs. time for plasma control and plasma in the presence of 1mcM HC-025s-IOC.

Changes in certain parameters measured in the thrombin generation tests in the presence of different concentrations of the compound HC-020s-IOC in plasma are reviewed below by way of example (see: Table 3). FIG. 5 illustrates curves constructed for accumulation of a fluorescent product in a breakdown reaction between a fluorogenic substrate and thrombin resulting from plasma clotting registered directly by a recorder (conventional fluorescence units have been converted into absolute AMC concentrations using ready calibrations prepared in advance). FIG. 6 shows kinetic profiles of thrombin concentration changes over the course of the experiment measured by differentiating the curves of FIG. 5. Reductions in thrombin potential and increase in the time needed to reach the maximum point on the thrombin generation curve with growth in inhibitor concentration in the system are shown in FIG. 7 and FIG. 8, respectively. These results show that plasma clotting slows down significantly with growth in the concentration of the test compound (HC-020s-IOC). The concentration of the compound that caused a 50% reduction in endogenous thrombin potential ($IC_{50}$) was found to be 0.9 mcM. This compound is, therefore, a strong anticoagulant:

The next three figures illustrate changes in the spatial clot growth dynamics in the presence of the compound HC-025s-IOC. FIG. 9 and FIG. 10 show light scattering profiles registered while clotting went on in the initial normal plasma and in the same plasma in the presence of 1 mcM of this compound, respectively. FIG. 11 shows growth in the clot size (as distance from the activator over which the clot spreads) versus time for plasma control and plasma in the presence of 1 mcM of the compound HC-025s-IOC. Comparison between the curves obtained also shows that the compound HC-025s-IOC present in plasma inhibits clotting.

Examples illustrating the anticoagulant effect of some of the newly synthesized compounds are given in Table 3.

EXAMPLE 7

Intensification of Clotting with Dilution of Normal Donor Blood with a Crystalloidal Plasma-Substituting Solution (NaCl 0.9%) and its Correction by Adding Various Concentrations of the Thrombin Activity Inhibiting Compound HC-025s-IOC to the Substituting Solution Donor blood prepared on a 3.8% sodium citrate at a 9:1 ratio of blood to citrate (20 ml) was centrifuged for 15 minutes at 1,300 g. Some of the platelet-poor plasma (PPP) was centrifuged for another 10 minutes at 10,000 g to obtain a platelet-free plasma (PFP). The PFP thus produced was then used for measuring the endogenous thrombin potential.

PFP was diluted at a ratio of 1.5, 2, 3 and 4 with either transfusion-grade physiological saline (NaCl 0.9%) or with the same solution containing additionally a thrombin inhibitor HC-025s-IOC (at concentrations of 0.25, 0.5 or 1 mcM). For constant concentration of $Ca^{+2}$ to be maintained through the tests after recalcification, sodium citrate concentration was maintained constant in all plasma dilutions to be identical to the concentration in initial undiluted plasma, for which purpose the initial plasma-substituting solutions used to dilute the plasma were first mixed with 3.8% sodium citrate similarly with initial blood at a 9:1 solution to citrate ratio.

The plasma sample used in the above-described ETP measurement method was always diluted at a 1.5 ratio throughout. An opportunity must be provided to measure ETP in undiluted plasma in experiments to dilute plasmas with PSS. Accordingly, a specialized methodology was developed to measure ETP in these experiments without actually diluting plasma during measurement. To take measurements, 200 microliters of plasma samples (undiluted PSS or PSS diluted a desired number of times) was placed into the cells of a 96-hole board to conduct measurements. Next, 2 microliters of a fluorogenic substrate solution in DMSO (at a starting concentration of 30.75 mM) was added to each cell. As clotting started, 3 microliters of an activator was added to each cell. The activator solution was prepared from a standard thromboplastin used for measuring prothrombin time (from Renam company, Russia), diluted 20 times with a buffer containing 20 mM of HEPES, 140 mM of NaCl and 1.235 M of $CaCl_2$, at pH 7.5. Measurement was then conducted by the method described previously. Endogenous thrombin potential was measured for each of the diluted plasmas in the presence of different concentrations of HC-025s-IOC.

Figure 12:
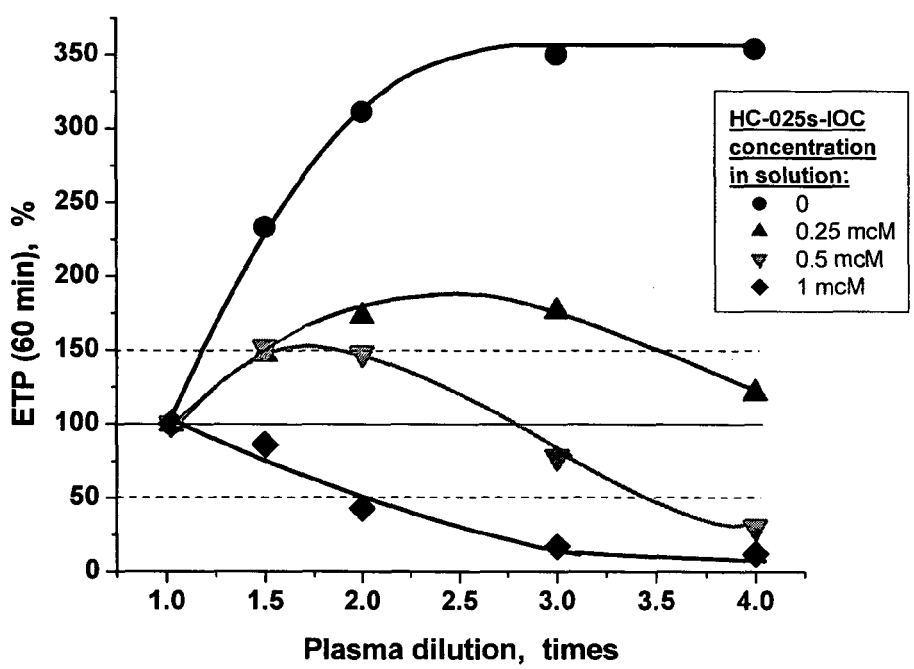
FIG. 12. Endogenous thrombin potential (ETP) measurements in a series of plasma dilutions with a NaCl (0.9%) solution containing different inhibitor concentrations.

FIG. 12 shows the results of ETP measurements in a series of plasma dilutions with a NaCl (0.9%) solution containing different inhibitor concentrations. Obviously, as plasma is gradually diluted with a substituting solution in the absence of added inhibitor, the endogenous thrombin potential grows significantly, which is indication of clotting intensifying in these conditions. In particular, ETP changing by as little as 20% is considered a thrombosis risk factor (Hemker H C, Al Dieri R, Beguin S. Thrombin generation assays: accruing clinical relevance. Curr. Opin. Hematol. 2004, 11(3):170-175). In our experiments, though, with initial plasma diluted at a ratio of 1.5 to 4, a maximum ETP increase varied from 1.5- to over 4-fold for different plasmas. Addition of an inhibitor does not fully neutralize the clotting intensification effect because of plasma dilutions, but adjusts it significantly, reducing ETP readings for different plasma dilutions. Moreover, HC-025s-IOC concentrations of 0.25-0.5 mcM in the solutions produce curves in which ETP readings for different plasma dilutions are the closest thing to normal.

TABLE 1

Mass-spectrometric parameters and the computed scoring functions for the thrombin inhibitors synthesized by the methods described in Examples 1-4

| Nos. (Molecular weight) | Chemical formula | Ion mass $(M+1)^+$ | Scoring function kcal/mol |
|---|---|---|---|
| 1 | | 399 | −6.51 |
| 2 | | 413 | −6.60 |
| 3 | | 413 | −6.42 |
| 4 | | 383 | −5.51 |
| 5 | | 369 | −5.86 |
| 6 | | 463 | −6.60 |
| 7 | | 399 | −6.81 |

TABLE 1-continued
Mass-spectrometric parameters and the computed scoring functions for the thrombin inhibitors synthesized by the methods described in Examples 1-4
| Nos. (Molecular weight) | Chemical formula | Ion mass (M + 1)+ | Scoring function kcal/mol |
|---|---|---|---|
| 8 | 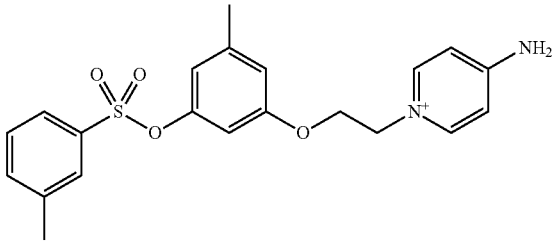 [SMILES: Cc1cc(OCC[n+]2ccc(N)cc2)cc(OS(=O)(=O)c2cccc(C)c2)c1] | 399 | −6.92 |
| 9 | 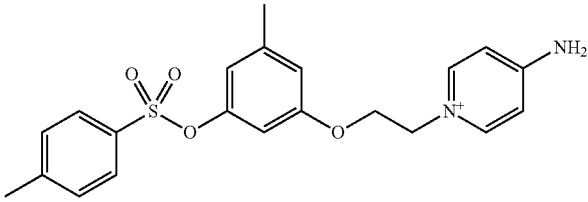 [SMILES: Cc1ccc(S(=O)(=O)Oc2cc(C)cc(OCC[n+]3ccc(N)cc3)c2)cc1] | 399 | −6.75 |
| 10 | 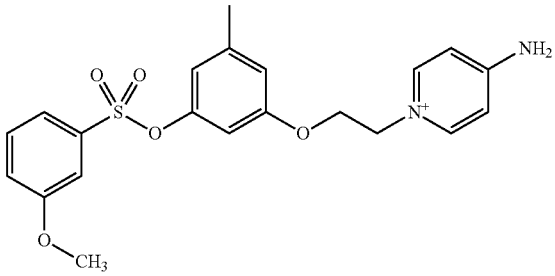 [SMILES: COc1cccc(S(=O)(=O)Oc2cc(C)cc(OCC[n+]3ccc(N)cc3)c2)c1] | 415 | −6.93 |
| 11 | 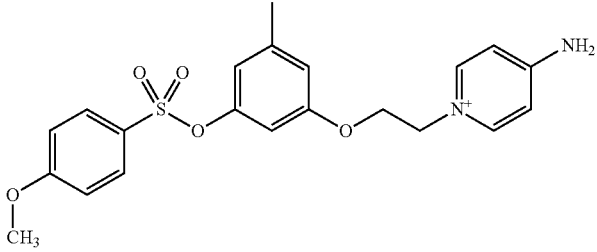 [SMILES: COc1ccc(S(=O)(=O)Oc2cc(C)cc(OCC[n+]3ccc(N)cc3)c2)cc1] | 415 | −7.02 |
| 12 | 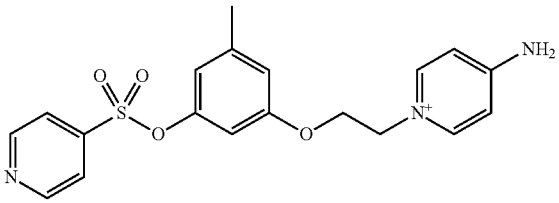 [SMILES: Cc1cc(OCC[n+]2ccc(N)cc2)cc(OS(=O)(=O)c2ccncc2)c1] | 386 | −6.73 |
| 13 | 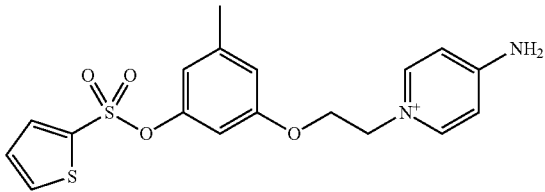 [SMILES: Cc1cc(OCC[n+]2ccc(N)cc2)cc(OS(=O)(=O)c2cccs2)c1] | 391 | −6.92 |

TABLE 1-continued
Mass-spectrometric parameters and the computed scoring functions for the thrombin inhibitors synthesized by the methods described in Examples 1-4
| Nos. (Molecular weight) | Chemical formula | Ion mass $(M + 1)^+$ | Scoring function kcal/mol |
|---|---|---|---|
| 14 | 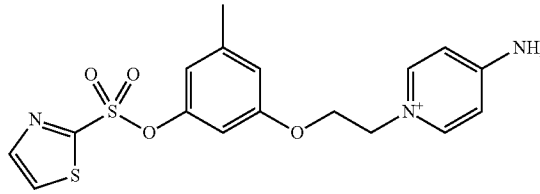 | 392 | −6.45 |
| 15 | 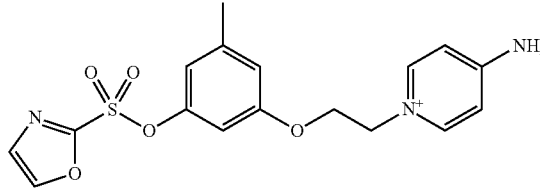 | 376 | −6.21 |
| 16 | 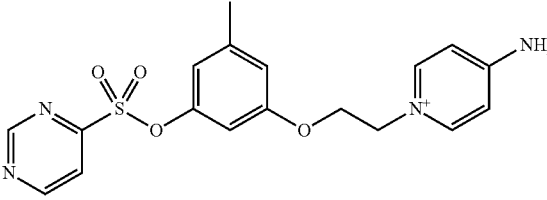 | 387 | −6.45 |
| 17 | 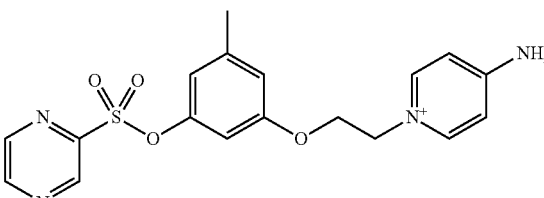 | 387 | −6.51 |
| 18 | 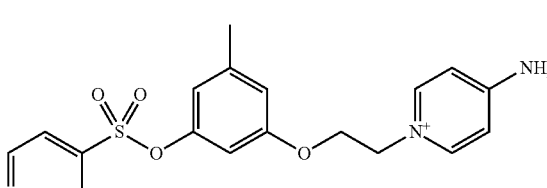 | 387 | −6.43 |
| 19 | 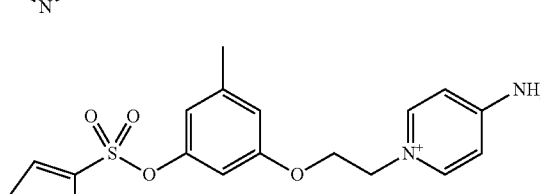 | 375 | −6.67 |
| 20 | 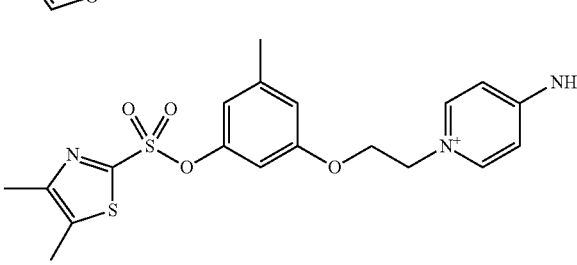 | 420 | −6.93 |

TABLE 1-continued

Mass-spectrometric parameters and the computed scoring functions for the thrombin inhibitors synthesized by the methods described in Examples 1-4

| Nos. (Molecular weight) | Chemical formula | Ion mass $(M + 1)^+$ | Scoring function kcal/mol |
|---|---|---|---|
| 21 | | 424 | −7.23 |
| 22 | | 425 | −7.12 |
| 23 | | 441 | −7.43 |
| 24 | | 370 | −7.01 |
| 25 | | 384 | −7.04 |
| 26 | | 442 | −7.12 |

TABLE 1-continued
Mass-spectrometric parameters and the computed scoring functions for the thrombin inhibitors synthesized by the methods described in Examples 1-4
| Nos. (Molecular weight) | Chemical formula | Ion mass $(M+1)^+$ | Scoring function kcal/mol |
|---|---|---|---|
| 27 | 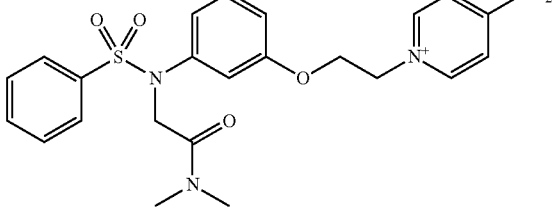 | 455 | −7.15 |
| 28 | 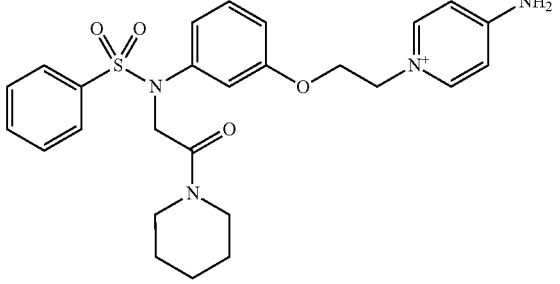 | 495 | −7.21 |
| 29 | 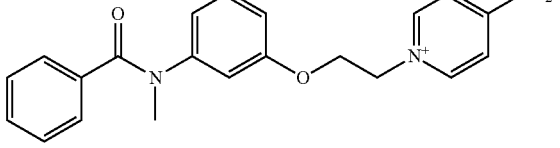 | 348 | −6.23 |
| 30 | 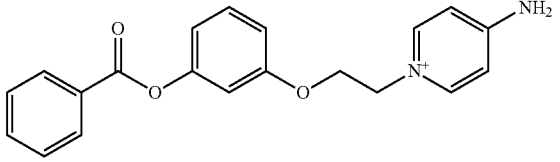 [SMILES: Nc1cc[n+](CCOc2cccc(OC(=O)c3ccccc3)c2)cc1] | 335 | −6.13 |
| 31 | 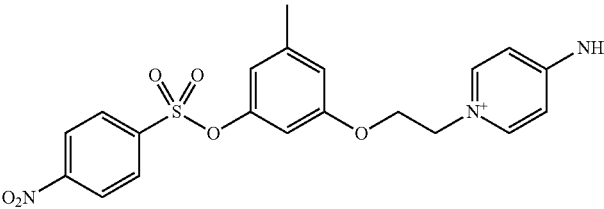 | 430 | −6.56 |
| 32 | 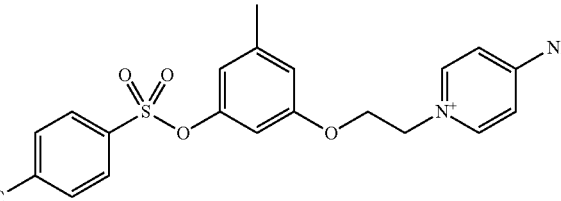 | 410 | −6.71 |

TABLE 1-continued

Mass-spectrometric parameters and the computed scoring functions for the thrombin inhibitors synthesized by the methods described in Examples 1-4

| Nos. (Molecular weight) | Chemical formula | Ion mass $(M + 1)^+$ | Scoring function kcal/mol |
|---|---|---|---|
| 33 | | 401 | −6.33 |
| 34 | | 443 | −6.84 |
| 35 | | 456 | −6.82 |
| 36 | | 428 | −6.51 |
| 37 | | 443 | −6.92 |
| 38 | | 456 | −7.12 |

TABLE 1-continued

Mass-spectrometric parameters and the computed scoring functions for the thrombin inhibitors synthesized by the methods described in Examples 1-4

| Nos. (Molecular weight) | Chemical formula | Ion mass $(M + 1)^+$ | Scoring function kcal/mol |
|---|---|---|---|
| 39 | | 386 | −5.45 |

TABLE 2

Mass-spectrometric parameters and the computed scoring functions for the thrombin inhibitors synthesized by the method described in Example 5

| Nos. (Molecular weight) | Chemical formula | Ion mass $(M + 1)^+$ | Scoring function kcal/mol |
|---|---|---|---|
| 1 | | 436 | −6.63 |
| 2 | | 450 | −6.41 |
| 3 | | 450 | −6.45 |

TABLE 2-continued
Mass-spectrometric parameters and the computed scoring functions for the thrombin inhibitors synthesized by the method described in Example 5
| Nos. (Molecular weight) | Chemical formula | Ion mass (M + 1)+ | Scoring function kcal/mol |
|---|---|---|---|
| 4 | 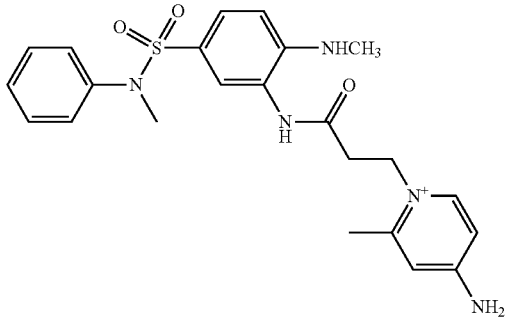 [SMILES: CNc1ccc(S(=O)(=O)N(C)c2ccccc2)cc1NC(=O)CC[n+]1ccc(N)cc1C] | 454 | −6.83 |
| 5 | 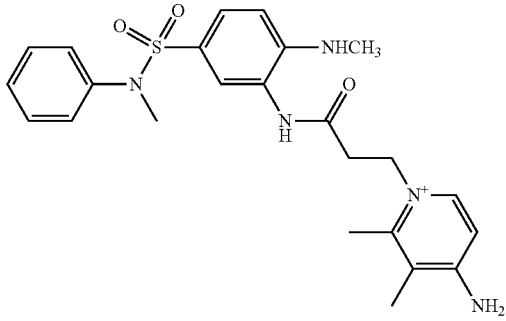 [SMILES: CNc1ccc(S(=O)(=O)N(C)c2ccccc2)cc1NC(=O)CC[n+]1ccc(N)c(C)c1C] | 468 | −6.54 |
| 6 | 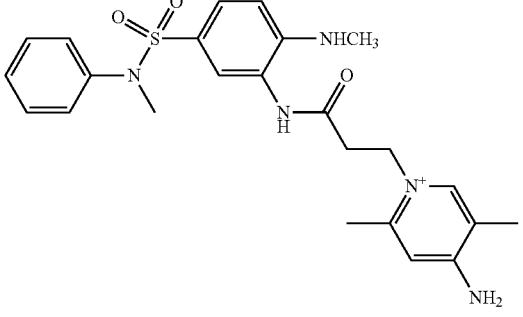 | 468 | −6.42 |
| 7 | 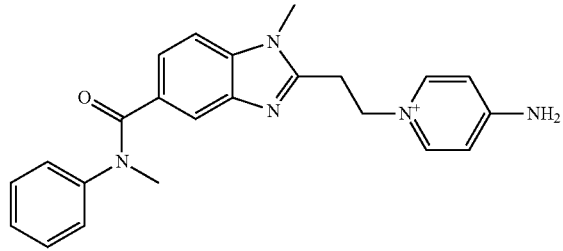 [SMILES: CN(C(=O)c1ccc2c(c1)nc(CC[n+]1ccc(N)cc1)n2C)c1ccccc1] | 386 | −5.93 |
| 8 | 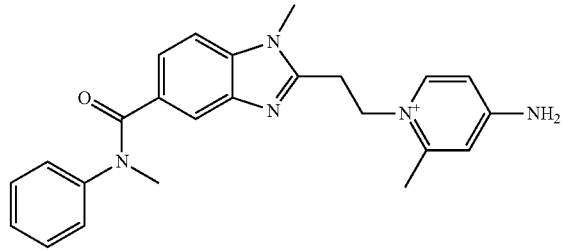 [SMILES: Cc1cc(N)cc[n+]1CCc1nc2cc(C(=O)N(C)c3ccccc3)ccc2n1C] | 400 | −5.63 |

TABLE 2-continued
Mass-spectrometric parameters and the computed scoring functions for the thrombin inhibitors synthesized by the method described in Example 5
| Nos. (Molecular weight) | Chemical formula | Ion mass $(M + 1)^+$ | Scoring function kcal/mol |
|---|---|---|---|
| 9 | 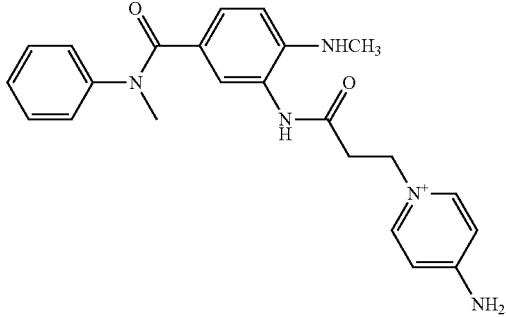 [SMILES: CNc1ccc(C(=O)N(C)c2ccccc2)cc1NC(=O)CC[n+]1ccc(N)cc1] | 404 | −6.21 |

TABLE 3

Examples illustrating anticoagulant effect and acute toxicity levels (LD$_{50}$) for a series of newly synthesized compounds

| Nos. (Molecular weight) | Compound structure | Estimate of ΔG for binding, kcal/mol | Compound concentration | Inhibition of endogenous thrombin potential, % | Thrombin time/Control thrombin time, sec | Clot growth rate inhibition, % | Toxicity, LD$_{50}$ (mice), mg/kg |
|---|---|---|---|---|---|---|---|
| HC-013s-IOC (Mw = 540) | 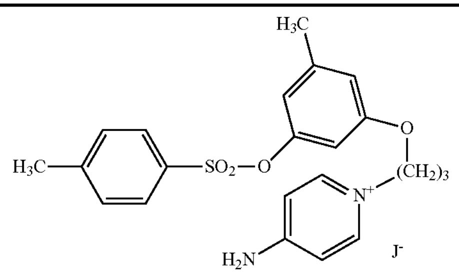 | −6.83 | 0.069 mM | 35.4 | | | |
| | | | 0.138 mM | 48.1 | | | |
| | | | 0.2 mM | | 115 ± 7/16 ± 3 | 19 | 125.0 ± 10 |
| | | | 0.25 mM | 58.3 | | | |
| | | | 0.276 mM | 59.4 | | | |
| | | | 0.345 mM | 68.5 | | | |
| | | | 0.69 mM | 95.0 | >300/16 ± 3 | 16 | |
| | | | 1.0 mM | IC$_{50}$ = 0.16 mM | | | |
| | | | 1.38 mM | | | | |
| HC-016s-IOC (Mw = 526) | 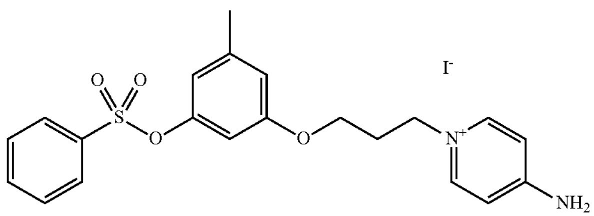 [SMILES: Cc1cc(OCCC[n+]2ccc(N)cc2)cc(OS(=O)(=O)c2ccccc2)c1 ; [I-]] | −6.42 | 10 mcM | 31.8 | | | |
| | | | 0.1 mM | 38.8 | | | |
| | | | 0.25 mM | 75.1 | 68 ± 2/20 ± 1 | 18 | |
| | | | 0.357 mM | 100 | | | |
| | | | 0.5 mM | IC$_{50}$ ≈ 0.24 mM | | | |
| | | | 0.714 mM | | | | |
| HC-017s-IOC (Mw = 532) | 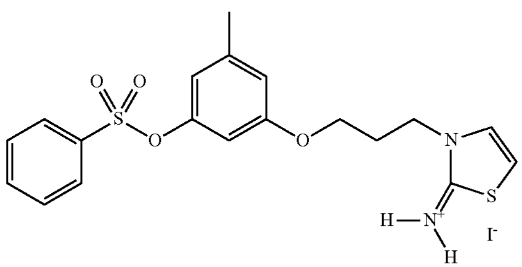 [SMILES: Cc1cc(OCCCn2ccsc2=[NH2+])cc(OS(=O)(=O)c2ccccc2)c1 ; [I-]] | −5.94 | 200 nM | 3.2 | | | |
| | | | 7.1 mcM | 23.3 | | | |
| | | | 14.3 mcM | 42.2 | 72 ± 1/20 ± 1 | 43 | >199 (0.9% NaCl) |
| | | | 20 mcM | 74.3 | | | |
| | | | 40 mcM | IC$_{50}$ = 24.8 mcM | >240/20 ± 1 | | |
| | | | 200 mcM | | | | |

TABLE 3-continued

Examples illustrating anticoagulant effect and acute toxicity levels ($LD_{50}$) for a series of newly synthesized compounds

| Nos. (Molecular weight) | Compound structure | Estimate of ΔG for binding, kcal/mol | Compound concentration | Inhibition of endogenous thrombin potential, % | Thrombin time/Control thrombin time, sec | Clot growth rate inhibition, % | Toxicity, $LD_{50}$ (mice), mg/kg |
|---|---|---|---|---|---|---|---|
| HC-018s-IOC (Mw = 508) | [structure] | −5.89 | 200 nM<br>6.5 mcM<br>7.1 mcM<br>13 mcM<br>4.3 mcM<br>26 mcM<br>50 mcM<br>52 mcM<br>104 mcM | 49.9<br>46.6<br>66.8<br>77.4<br>90.4<br>98.6<br>100<br>$IC_{50}$ = 7.9 mcM | 168 ± 8/20 ± 1 | 40 | <441.11 (0.9% NaCl + cremophor 20%) |
| HC-019s-IOC (Mw = 512) | [structure] | −6.56 | 5 nM<br>10 nM<br>25 nM<br>50 nM<br>250 nM<br>0.5 mcM<br>1.25 mcM<br>1.38 mcM<br>2.41 mcM<br>3.45 mcM<br>6.25 mcM<br>6.9 mcM<br>13 mcM<br>26 mcM<br>66.5 mcM<br>133 mcM | 15.3<br>31.1<br>47.5<br>87.5<br>88.0<br>94.3<br>90.6<br>99.4<br>93.9<br>$IC_{50}$ = 0.25 mcM | 43 ± 10/20 ± 1<br>111 ± 20/20 ± 1 | 24<br>26<br>43<br>46<br>100<br>100 | >278.33 (0.9% NaCl + cremophor 20%) |
| HC-020s-IOC (Mw = 494) | [structure] | −6.12 | 50 nM<br>500 nM<br>690 nM<br>1.38 mcM<br>6.9 mcM<br>13.8 mcM<br>34.5 mcM<br>50 mcM<br>100 mcM<br>200 mcM<br>500 mcM | 40.5<br>67.9<br>89.1<br>92.2<br>100<br>$IC_{50}$ = 0.9 mcM | 39 ± 1/20 ± 1<br>196 ± 11/20 ± 1 | 16<br>30<br>95<br>100 | >1111.11 (0.9% NaCl + cremophor 20%) |

TABLE 3-continued

Examples illustrating anticoagulant effect and acute toxicity levels (LD$_{50}$) for a series of newly synthesized compounds

| Nos. (Molecular weight) | Compound structure | Estimate of ΔG for binding, kcal/mol | Compound concentration | Inhibition of endogenous thrombin potential, % | Thrombin time/Control thrombin time, sec | Clot growth rate inhibition, % | Toxicity, LD$_{50}$ (mice), mg/kg |
|---|---|---|---|---|---|---|---|
| HC-023s-IOC (Mw = 560.5) | [structure] | −6.61 | 10 mcM<br>20 mcM<br>50 mcM<br>200 mcM<br>0.5 mM | 22.3<br>34.5<br>57.9<br>99.2<br>IC$_{50}$ = 40 mcM | | 30 | |
| HC-024s-IOC (Mw = 534.5) | [structure] | −5.54 | 10 mcM<br>20 mcM<br>50 mcM<br>200 mcM | 53.4<br>66.5<br>92.6<br>100<br>IC$_{50}$ = 9.3 mcM | | 10 | |
| HC-025s-IOC (Mw = 546.5) | [structure] | −6.81 | 96 nM<br>192 nM<br>385 nM<br>769 nM<br>1 mcM | 25.4<br>40.6<br>65.5<br>99.7<br>IC$_{50}$ = 0.26 mcM | | 40 | |

TABLE 3-continued

Examples illustrating anticoagulant effect and acute toxicity levels ($LD_{50}$) for a series of newly synthesized compounds

| Nos. (Molecular weight) | Compound structure | Estimate of ΔG for binding, kcal/mol | Compound concentration | Inhibition of endogenous thrombin potential, % | Thrombin time/Control thrombin time, sec | Clot growth rate inhibition, % | Toxicity, $LD_{50}$ (mice), mg/kg |
|---|---|---|---|---|---|---|---|
| HC-026s-IOC (Mw = 542.5) | 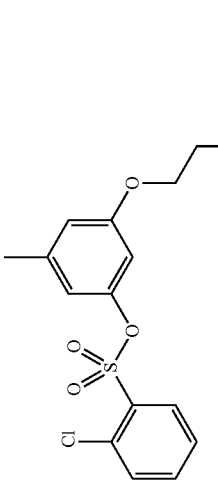 | −5.63 | 770 nM<br>1.54 mcM<br>3.85 mcM<br>7.69 mcM<br>50 mcM | 27.5<br>34.0<br>49.0<br>65.7<br>$IC_{50}$ = 4.1 mcM | | 17 | |
| HC_028s_IOC (Mw = 492) | 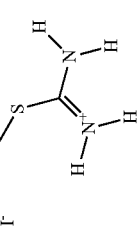 | | 0.7 mcM<br>14.8 mcM<br>25 mcM<br>50 mcM<br>1 mM<br>2.5 mM | 13<br>81<br>~$IC_{50}$ = 9.0 mcM | | 1<br>60 | 257.27 ± 30.97 (NaCl 0.9% + cremophor 20%) |

TABLE 3-continued

Examples illustrating anticoagulant effect and acute toxicity levels (LD$_{50}$) for a series of newly synthesized compounds

| Nos. (Molecular weight) | Compound structure | Estimate of ΔG for binding, kcal/mol | Compound concentration | Inhibition of endogenous thrombin potential, % | Thrombin time/Control thrombin time, sec | Clot growth rate inhibition, % | Toxicity, LD$_{50}$ (mice), mg/kg |
|---|---|---|---|---|---|---|---|
| HC_029s_IOC (Mw = 544.5) | 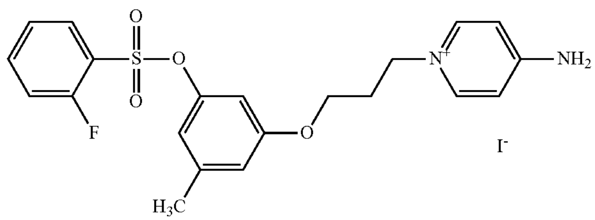 | −5.85 | 1.5 mcM<br>14.8 mcM<br>148 mcM<br>1 mM | 0<br>33<br>85<br>IC$_{50}$ = 27 mcM | | 56 | |
| HC_030s_IOC (Mw = 518.5) | 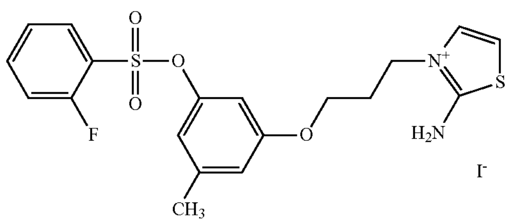 | −6.07 | 3 mcM<br>14.8 mcM<br>2 mM | 27<br>76<br>~IC$_{50}$ = 8.6 mcM | | 9 | |
| HC_031s_IOC (Mw = 492) | 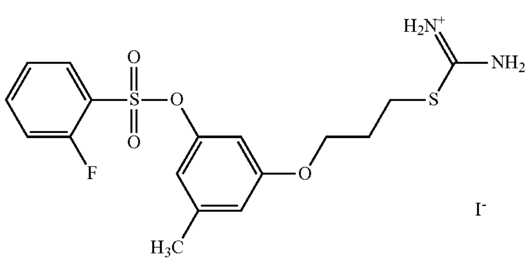 [SMILES: Cc1cc(OCCCSC(N)=[NH2+])cc(OS(=O)(=O)c2ccccc2F)c1 ; [I-]] | −5.81 | 0.5 mcM<br>1 mcM<br>4 mcM<br>1 mM | 26.28<br>45.80<br>97.26<br>IC$_{50}$ = 1.24 mcM | | 51 | |

TABLE 3-continued

Examples illustrating anticoagulant effect and acute toxicity levels (LD$_{50}$) for a series of newly synthesized compounds

| Nos. (Molecular weight) | Compound structure | Estimate of ΔG for binding, kcal/mol | Compound concentration | Inhibition of endogenous thrombin potential, % | Thrombin time/Control thrombin time, sec | Clot growth rate inhibition, % | Toxicity, LD$_{50}$ (mice), mg/kg |
|---|---|---|---|---|---|---|---|
| HC_032s_IOC (Mw = 555.5) | 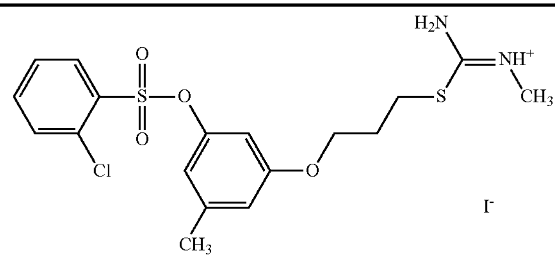 | −5.42 | 29.6 mcM<br>74 mcM<br>296 mcM<br>1 mM | 57<br>75<br>98<br>IC$_{50}$ = 25.2 mcM | | 31 | |
| HC_033s_IOC (Mw = 541.5) | 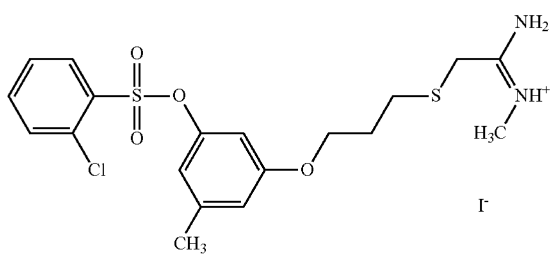 [SMILES: C/[NH+]=C(/N)CSCCCOc1cc(C)cc(OS(=O)(=O)c2ccccc2Cl)c1 ; [I-]] | −5.61 | 0.6 mcM<br>3.0 mcM<br>5.9 mcM<br>59 mcM<br>0.5 mM<br>1 mM | 52<br>80<br>87<br>88<br>IC$_{50}$ = 0.527 mcM | | 81<br>100 | |
| HC_036s_IOC (Mw = 526) | 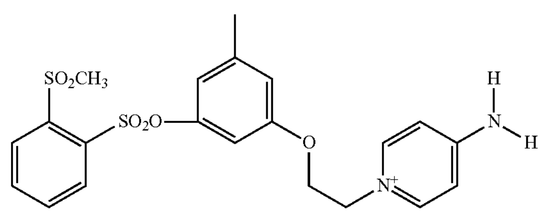 | −6.6 | 185.2 nM<br>370.4 nM<br>500 nM<br>740.4 nM<br>1 mcM<br>2 mcM<br>80 mcM<br>100 mcM<br>200 mcM | 43.46<br>93.73<br>88.83<br>99.88<br>96.36<br>99.60<br>IC$_{50}$ = 157.5 nM | | 0<br>16<br>97<br>99 | |

TABLE 3-continued

Examples illustrating anticoagulant effect and acute toxicity levels (LD$_{50}$) for a series of newly synthesized compounds

| Nos. (Molecular weight) | Compound structure | Estimate of ΔG for binding, kcal/mol | Compound concentration | Inhibition of endogenous thrombin potential, % | Thrombin time/Control thrombin time, sec | Clot growth rate inhibition, % | Toxicity, LD$_{50}$ (mice), mg/kg |
|---|---|---|---|---|---|---|---|
| HC_037s_IOC (Mw = 530.35) | 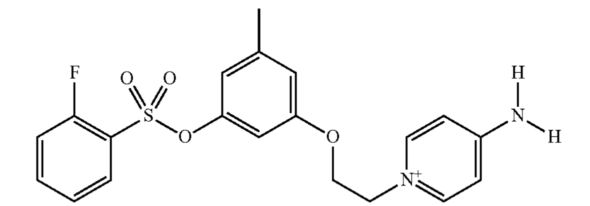 [SMILES: Cc1cc(OCC[n+]2ccc(N)cc2)cc(OS(=O)(=O)c2ccccc2F)c1] | −6.49 | 148 nM<br>1.48 mcM<br>14.8 mcM<br>100 mcM<br>200 mcM | 75<br>93<br>97<br>~IC$_{50}$ = 0.1 mcM | | 64<br>85 | |
| HC_038s_IOC (Mw = 529.39) | 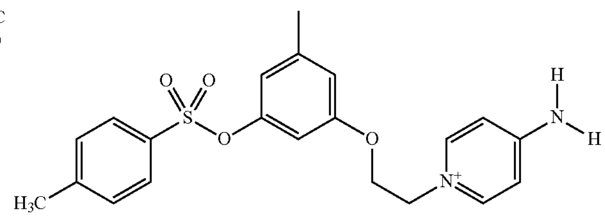 | −6.75 | 0.14 mcM<br>2.5 mcM<br>13.7 mcM<br>0.2 mM<br>1.4 mM | 33<br>90<br>99<br>~IC$_{50}$ = 4.0 mcM | | 66 | |
| HC_039s_IOC (Mw = 546.81) | 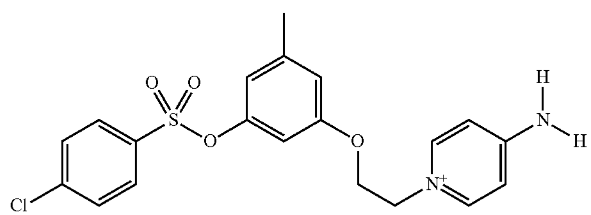 [SMILES: Cc1cc(OCC[n+]2ccc(N)cc2)cc(OS(=O)(=O)c2ccc(Cl)cc2)c1] | −7.03 | 0.15 mcM<br>0.74 mcM<br>1.4 mcM<br>13.8 mcM<br>80 mcM<br>200 mcM<br>1.4 mM | 50<br>69<br>89<br>92<br>97<br>IC$_{50}$ = 0.15 mcM | | 4<br>60 | |
| HC_040s_IOC (Mw = 572.46) | 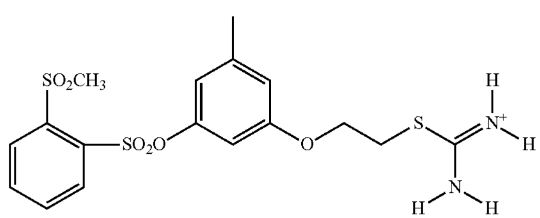 | −5.48 | 460 nM<br>930 nM<br>1.85 mcM<br>3.70 mcM<br>7.41 mcM<br>100 mcM<br>200 mcM | 39.43<br>54.14<br>80.51<br>95.16<br>100<br>IC$_{50}$ = 0.8 mcM | | 65<br>76 | |

TABLE 3-continued

Examples illustrating anticoagulant effect and acute toxicity levels (LD$_{50}$) for a series of newly synthesized compounds

| Nos. (Molecular weight) | Compound structure | Estimate of ΔG for binding, kcal/mol | Compound concentration | Inhibition of endogenous thrombin potential, % | Thrombin time/Control thrombin time, sec | Clot growth rate inhibition, % | Toxicity, LD$_{50}$ (mice), mg/kg |
|---|---|---|---|---|---|---|---|
| HC_041s_IOC (Mw = 405.5) | 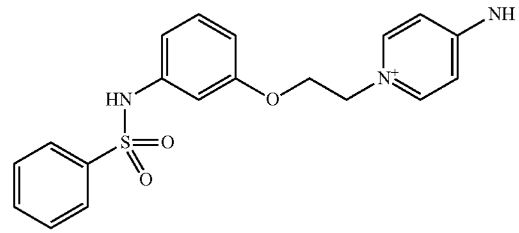 [SMILES: Nc1cc[n+](CCOc2cccc(NS(=O)(=O)c3ccccc3)c2)cc1] | −7.01 | 7.4 nM<br>0.7 mcM<br>3.75 mcM<br>7.4 mcM<br>37 mcM<br>100 mcM<br>200 mcM | 32<br>56<br>55<br>85<br>96<br><br>IC$_{50}$ = 1.6 mcM | | 36<br>67 | |
| HC_045s_IOC (Mw = 520.5) | 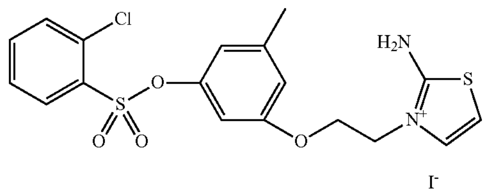 [SMILES: Cc1cc(OCC[n+]2ccsc2N)cc(OS(=O)(=O)c2ccccc2Cl)c1 ; [I-]] | −5.88 | 1.85 mcM<br>3.70 mcM<br>18.52 mcM<br>37.04 mcM<br>74.07 mcM<br>100 mcM<br>200 mcM | 23.08<br>37.42<br>52.41<br>67.63<br>92.00<br><br>IC$_{50}$ = 16 mcM | | 0<br>63 | |
| HC_046s_IOC (Mw = 528.5) | 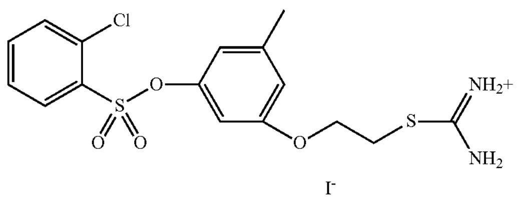 [SMILES: Cc1cc(OCCSC(N)=[NH2+])cc(OS(=O)(=O)c2ccccc2Cl)c1 ; [I-]] | −6.02 | 74 nM<br>185.2 nM<br>370.4 nM<br>740.7 nM<br>1.852 mcM<br>100 mcM | 28.04<br>57.15<br>80.39<br>92.08<br>98.68<br>IC$_{50}$ = 160 mcM | | 68 | |
| HC_047s_IOC (Mw = 513.35) | 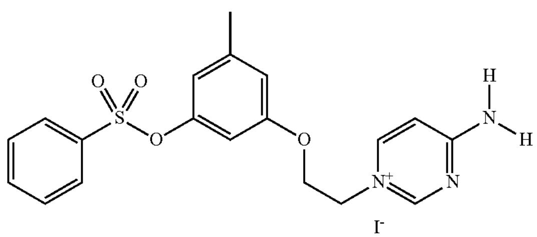 [SMILES: Cc1cc(OCC[n+]2ccc(N)nc2)cc(OS(=O)(=O)c2ccccc2)c1 ; [I-]] | −5.45 | 1.85 mcM<br>3.70 mcM<br>18.52 mcM<br>37.04 mcM<br>40 mcM<br>74.07 mcM<br>200 mcM | 41.86<br>64.02<br>99.18<br>100<br><br>100<br>IC$_{50}$ = 2.5 mcM | | 44<br>48 | |

What is claimed is:

1. A compound of the general structural formula (I) or a pharmaceutically acceptable salt thereof:

A-B—C    (I)

wherein C is chosen from the group consisting of the structures:

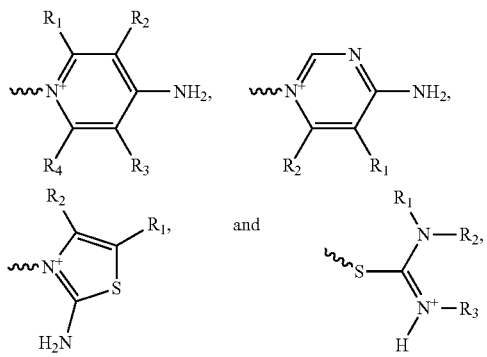

wherein $R_1$, $R_2$, $R_3$, and $R_4$ are independent from one another, and are hydrogen or $C_{1-6}$ alkyl;

B is —$(CH_2)_n$—, wherein n is an integer from 2 to 5; and

A is selected from the group consisting of the structures:

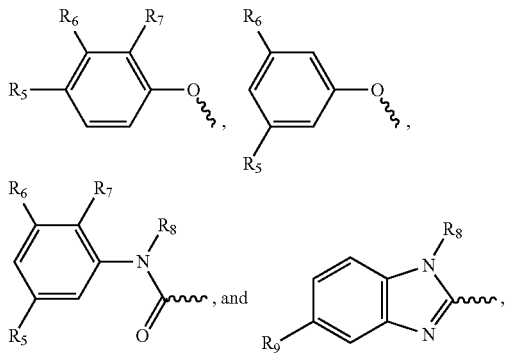

wherein $R_5$ is selected from the group consisting of $CH_2NR_{10}R_{11}$, and $CH(CH_3)NR_{10}R_{11}$,

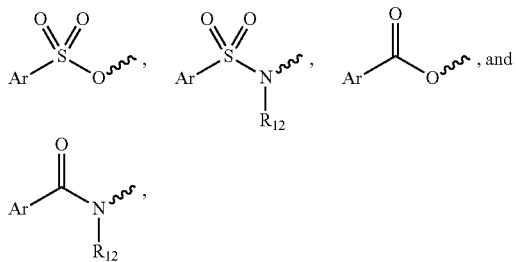

R6 and R7 are independently selected from the group consisting of hydrogen, C1-6 alkyl, C1-6 alkoxy and halogen;

$R_8$ is hydrogen or $C_{1-6}$ alkyl;

$R_9$ is selected from the group consisting of:

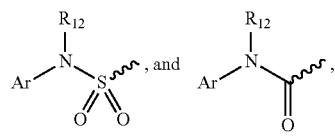

$R_{10}$ and $R_{12}$ are independently from each other and are selected from the group consisting of hydrogen, $C_{1-6}$ alkyl, $(CH_2)_m COOR_{13}$, $(CH_2)_m CON(R_{13})_2$,

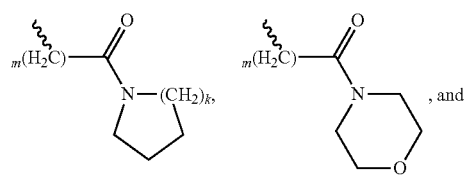

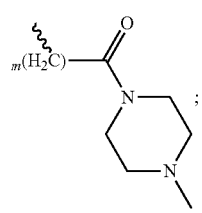

wherein m is an integer from 1 to 4, k is an integer from 1 to 3, $R_{13}$ is hydrogen or $C_{1-6}$ alkyl, $R_{11}$ is $C_{1-6}$ alkyl or Ar;

Ar is phenyl, pyridyl, oxazolyl, thiazolyl, thienyl, furanyl, pyrimidinyl, pyridazonyl, pyrazinyl, indolyl, benzofuranyl, or benzothiophenyl, having from one to five substituents selected from the group consisting of:

hydrogen, $C_{1-8}$ alkyl, $C_{1-6}$ alkoxy, halogen, $N(R_{13})_2$, OH, $NO_2$, CN, $COOR_{13}$, $CON(R_{13})_2$, and $SO_2R_{13}$.

2. A compound or pharmaceutically acceptable salt of claim 1, selected from the group consisting of:

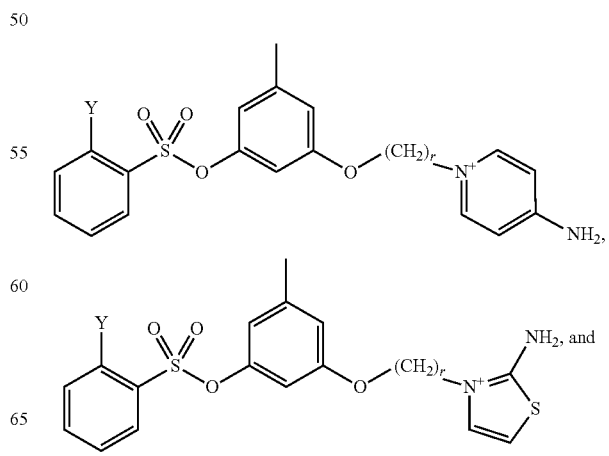

-continued

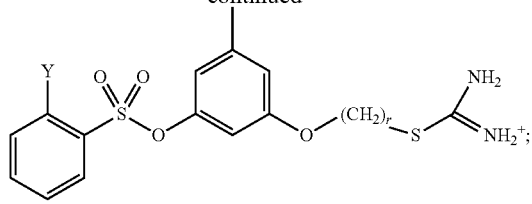

wherein Y is selected from the group consisting of hydrogen, halogen, $COOR_{13}$, $CON(R_{13})_2$, and $SO_2R_{13}$; and
r is an integer from 2 to 5.

3. The compound or pharmaceutically acceptable salt of claim 1, wherein C is:

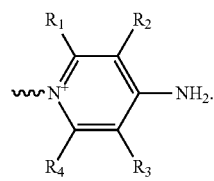

4. The compound or pharmaceutically acceptable salt of claim 1, wherein C is:

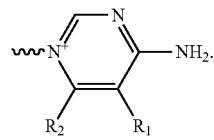

5. The compound or pharmaceutically acceptable salt of claim 1, wherein C is:

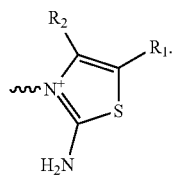

6. The compound or pharmaceutically acceptable salt of claim 1, wherein C is:

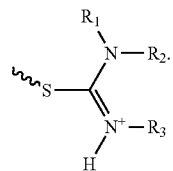

7. The compound or pharmaceutically acceptable salt of claim 1, wherein A is:

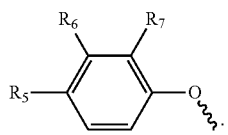

8. The compound or pharmaceutically acceptable salt of claim 1, wherein A is:

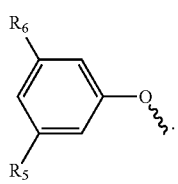

9. The compound or pharmaceutically acceptable salt of claim 1, wherein A is:

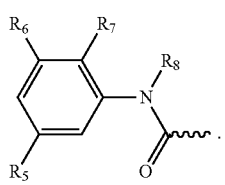

10. The compound or pharmaceutically acceptable salt of claim 1, wherein A is:

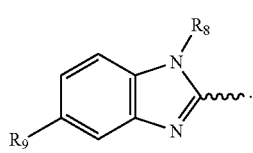

11. A pharmaceutical composition comprising a compound according to claim 1, or a salt thereof, and a pharmaceutically acceptable additive.

* * * * *